US008440640B2

(12) United States Patent
Vatner

(10) Patent No.: US 8,440,640 B2
(45) Date of Patent: May 14, 2013

(54) METHODS AND COMPOSITIONS FOR TREATING OBESITY AND RELATED DISORDERS

(75) Inventor: Stephen F. Vatner, New York, NY (US)

(73) Assignee: University of Medicine and Dentistry of New Jersey, Somerset, NJ (US)

( * ) Notice: Subject to any disclaimer, the term of this patent is extended or adjusted under 35 U.S.C. 154(b) by 180 days.

(21) Appl. No.: 13/129,586

(22) PCT Filed: Nov. 18, 2009

(86) PCT No.: PCT/US2009/006172
§ 371 (c)(1),
(2), (4) Date: May 26, 2011

(87) PCT Pub. No.: WO2010/059204
PCT Pub. Date: May 27, 2010

(65) Prior Publication Data
US 2011/0230435 A1 Sep. 22, 2011

Related U.S. Application Data

(60) Provisional application No. 61/199,715, filed on Nov. 18, 2008.

(51) Int. Cl.
*A01N 43/04* (2006.01)
*A61K 31/70* (2006.01)

(52) U.S. Cl.
USPC ............ 514/46; 514/43; 514/45; 514/47; 514/48

(58) Field of Classification Search .................. None
See application file for complete search history.

(56) References Cited

U.S. PATENT DOCUMENTS

| 5,872,104 | A | 2/1999 | Vermeulen et al. | 514/29 |
| 2003/0229010 | A1 | 12/2003 | Ekwuribe | 514/3 |
| 2006/0252774 | A1 | 11/2006 | Vatner | 514/263.2 |
| 2008/0274103 | A1 | 11/2008 | Vatner et al. | 424/133.1 |

OTHER PUBLICATIONS

Vannucci et al. The American Physiological Society (1989), pp. E871-E878.*
Dighe et al. The American Society for Clinical Invesitigation (1984), vol. 73, pp. 1013-1017.*
Balady, G. J. "Exercise Training in the Treatment of Heart Failure: What Is Achieved and How?" Annals of Internal Medicine 1998 30(1):61-65.
Fuller et al. "Mortality from Coronary Heart Disease and Stroke in Relation to Degree of Glycaemia: the Whitehall Study" British Medical Journal 1983 287:867-870.
Isakovic et al. "Brain to Blood Efflux Transport of Adenosine: Blood-brain Barrier Studies in the Rat" Journal of Neurochemistry 2004 90:272-286.

Iwamoto et al. "Motor Dysfunction in Type 5 Adenylyl Cyclase-null Mice" The Journal of Biological Chemistry 2003 278(19):16936-16940.
Iwase et al. "Neurally Mediated Cardiac Effects of Forskolin in Conscious Dogs" American Journal of Physiology 1996 271:H1473-H1482.
Iwatsubo et al. "Direct Inhibition of Type 5 Adenylyl Cyclase Prevents Myocardial Apoptosis without Functional Deterioration" The Journal of Biological Chemistry 2004 279(39):40938-40945.
Iwatsubo et al. "Drug Therapy Aimed at Adenylyl Cyclase to Regulate Cyclic Nucleotide Signaling" Endocrine, Metabolic & Immune Disorders—Drug Targets 2006 6:239-247.
Jefferson et al. "Amantadine and Rimantadine for Influenza A in Adults" Cochrane Database for Systematic Reviews 2006 2:CD001169.
Kleymann, G. "Novel Agents and Strategies to Treat Herpes Simplex Virus Infections" Expert Opinion on Investigational Drugs 2003 12(2):165-183.
Londos, C. and Wolff, J. "Two Distinct Adenosine-sensitive Sites on Adenylate Cyclase" Proceedings of the National Academy of Sciences USA 1977 74(12):5482-5486.
Massie, B. M. "Exercise Tolerance in Congestive Heart Failure. Role of Cardiac Function, Peripheral Blood Flow, and Muscle Metabolism and Effect of Treatment" The American Journal of Medicine 1988 84(3A):75-82.
Okumura et al. "Disruption of Type 5 Adenylyl Cyclase Enhances Desensitization of Cyclic Adenosine Monophosphate Signal and Increases Akt Signal with Chronic Catecholamine Stress" Circulation 2007 116:1776-1783.
Okumura et al. "Disruption of Type 5 Adenylyl Cyclase Gene Preserves Cardiac Function against Pressure Overload" Proceedings of the National Academy of Sciences USA 2003 100(17):9986-9990.
Onda et al. "Type-specific Regulation of Adenylyl Cyclase" The Journal of Biological Chemistry 2001 276(51):47785-47793.
Tesmer et al. "Molecular Basis for P-site Inhibition of Adenylyl Cyclase" Biochemistry 2000 39:14464-14471.
Tesmer et al. "Two-metal-ion Catalysis in Adenylyl Cyclase" Science 1999 285:756-760.
Toya et al. "Forskolin Derivatives with Increased Selectivity for Cardiac Adenylyl Cyclase" Journal of Molecular and Cellular Cardiology 1998 30:97-108.
Whitley, R. J. "The Past as Prelude to the Future: History, Status, and Future of Antiviral. Drugs" The Annals of Pharmacotherapy 1996 30(9):967-971.
Wohnsland et al. "Viral Determinants of Resistance to Treatment in Patients with Hepatitis C" Clinical Microbiology Reviews 2007 20(1):23-38.
Yan et al. "Type 5 Adenylyl Cyclase Disruption Increases Longevity and Protects Against Stress" Cell 2007 130:247-258.

* cited by examiner

*Primary Examiner* — Patrick Lewis
(74) *Attorney, Agent, or Firm* — Licata & Tyrrell P.C.

(57) ABSTRACT

The invention provides methods for, and compositions effective for, treating obesity, inhibiting weight gain, treating diabetes mellitus, inhibiting atherosclerosis and treating related disorders and conditions comprising administering a pharmaceutically effective amount of at least one compound capable of inhibiting AC5 to a patient. The compound capable of inhibiting AC5 may be administered singly or in combination with another agent. In some embodiments, the AC5 inhibiting compound is 9-β-D-arabinofuranosyladenine (AraAde). The compounds may be administered in an amount of about 1 to about 200 mg/kg/day, about 1 to about 100 mg/kg/day, about 10 to about 80 mg/kg/day, about 12 to about 40 mg/kg/day or about 15 to about 25 mg/kg/day. In some embodiments, the compound is administered orally.

12 Claims, 14 Drawing Sheets

Survival Rate

AC5 expression in adipose tissue

Heart  Adipose tissue

AC5 expression in diabetic mice

— 100 KD

Effect of high fat diet on glucose and triglyceride levels

LV function with ISO-challenge

*40 days of treatment, 84 days into HFD; test done with 1g/kg IP glucose

METHODS AND COMPOSITIONS FOR TREATING OBESITY AND RELATED DISORDERS

CROSS REFERENCE TO RELATED APPLICATIONS

This patent application is the National Stage of International Application No. PCT/US2009/006172, filed Nov. 18, 2009, which claims the benefit of priority from U.S. Provisional Application Ser. No. 61/199,715, filed Nov. 18, 2008, teachings of each of which are herein incorporated by reference in their entirety.

FIELD OF THE INVENTION

The invention relates to the use of Type 5 Adenylyl Cyclase (hereinafter "Type 5 AC" or "AC5") inhibitors to treat obesity and related disorders such as diabetes mellitus.

BACKGROUND OF THE INVENTION

AC is a 12-transmembrane protein that catalyzes the conversion of ATP to cAMP upon the stimulation of various G-protein coupled receptors such as β-adrenergic receptor (β-AR). Nine mammalian AC subtypes have been identified, and each subtype shows distinct tissue distributions, and biological and pharmacological properties (Iwatsubo et al., *Endocr Metab Immune Disord Drug Targets*. September 2006;6(3):239-247). Stimulation of G protein-coupled receptors induces binding of the stimulatory Gα subunit (Gsα) to AC, and enhances its catalytic activity to convert ATP into cAMP. cAMP regulates multiple downstream molecules, via protein kinase A (PKA) and exchange protein activated by cAMP (Epac).

AC5 is a major cardiac subtype of AC, which provides 20% of total AC activity in the heart, and recent studies including ours revealed its crucial role in progression of HF (Iwatsubo et al., *J Biol Chem*. Sep. 24, 2004;279(39):40938-40945; Okumura et al., *Circ Res*. Aug. 22, 2003 2003;93(4):364-371). AC5KO mice showed decreased myocardial apoptosis and preserved cardiac function in HF models induced by chronic pressure overload (Okumura et al. *Proceedings of the National Academy of Sciences*. 2003;100(17):9986-9990), chronic β-AR stimulation (Okumura et al., *Circulation*. 2007; 116(16):1776-1783) and aging (Yan et al., *Cell*. Jul. 27, 2007; 130(2):247-258). In all these HF models, myocardial apoptosis, which is a major cause for progression of HF, was significantly decreased in AC5KO, indicating that AC5 plays a central role in inducing apoptosis and subsequent development of HF. Moreover, AC5Tg showed decreased left ventricular ejection fraction (LVEF) and increased apoptosis in response to chronic pressure overload, indicating that AC5 accelerates the progression of HF by inducing myocardial apoptosis. These data strongly suggest that among mechanisms by which myocardial apoptosis occurs such as renin-angiotensin-aldosterone, death receptor and calcium signaling, sympathetic activity overdrive, particularly via stimulating AC5, plays a major role in inducing myocardial apoptosis and development of HF.

Classic inhibitors of AC, known as P-site inhibitors, have been studied since the 1970's. It was first thought that there was an adenosine-reactive site within intracellular domain of AC, the "P" site, which inhibits the catalytic activity of AC. In spite of their similar chemical structure to the substrate ATP, P-site inhibitors showed un- or non-competitive inhibition with respect to ATP, indicating little influence on molecules which have ATP-binding site (Londos et al., *Proc Natl Acad Sci U S A*. December 1977;74(12):5482-5486). Although it has been a very attractive idea to develop P-site inhibitors with enhanced AC subtype selectivity, few attempts have been successful due to the difficulties of experiments in which the selectivity of each AC isoforms can be examined in vitro. However, several groups including ours have developed such experimental systems using the baculovirus-based recombinant AC overexpression system (Iwatsubo et al., *J Biol Chem*. Sep. 24, 2004;279(39):40938-40945; Onda et al. *J Biol Chem*. Dec. 21, 2001;276(51):47785-47793).

9-β-D-arabinofuranosyladenine (AraAde) contains an adenosine-like structure where the adenine ring is essential not only for binding to the AC catalytic core but also for penetrating the plasma membrane (Iwatsubo et al. *J Biol Chem*. 2004;279(39):40938-40945, Onda et al. *J Biol Chem*. 2001;276(51):47785-47793. Tesmer et al. *Biochemistry*.2000;39(47):14464-14471. Tesmer et al. *Science*. 1999; 285(5428):756-760). For example, NKY80, which does not contain adenosine within its structure, showed moderate inhibition of purified AC5 protein in vitro, but it does not inhibit cAMP accumulation in cultured cardiac myocytes, indicating that the adenosine structure seems essential for penetrating the plasma membrane (Iwatsubo, et al. *J Biol Chem*.279(39): 40938-40945). In addition, adenosine hardly crosses through the blood-brain barrier (BBB) (Isakovic et al. *Journal of Neurochemistry*, 90(2):272-286.), having little influence on brain function; this is important because AC5 is also expressed in the striatum other than the heart, thus by passing BBB AC5 inhibitors may cause adverse effects in the brain.

Obesity is a disease in which excess body fat has accumulated to such an extent that health may be negatively affected. Many studies have shown an association between excessive body weight and various diseases, particularly cardiovascular diseases, diabetes mellitus type 2, sleep apnea, certain types of cancer, and osteoarthritis. As a result, obesity has been found to reduce life expectancy. Obesity is a global epidemic. As of 2005 the World Health Organization estimates that at least 400 million adults (9.8%) are obese. The United States has the highest rates of obesity in the developed world. It was reported in 2005 that about 119 million, or 64.5%, of US adults are either overweight or obese. Obesity is a public health problem because of its prevalence, costs and burdens. Obesity can be caused by dietary, behavioral and genetic factors. There have been several genes identified that are involved in the development of obesity.

Obesity is a complex disease influenced by diet, exercise, and a complex biology. Many peer-reviewed studies show that people who successfully complete weight loss program generally regain weight. Bariatric surgery to reduce the size of the stomach (gastric bypass surgery) is the only effective treatment for causing weight loss in morbid obese people. Two prescription drugs have been approved by the Food and Drug Administration (FDA) for long-term weight loss (Sibutramine and Orlistat, combined market $500 million). These drugs work in different ways, cause different side effects and only result in modest weight loss. Thus, discovery of novel obesity treatments is urgently needed to treat this epidemic.

Obesity in humans and in rodents is usually associated with high circulating leptin levels and leptin resistance. Leptin, the protein product of the ob gene, is predominantly secreted from white adipose tissue, and acts on the brain to regulate food in-take, energy expenditure, and neuroendocrine function. In obese (ob/ob) mice that lack functional leptin, recombinant leptin is highly effective at reversing obesity. However, most cases of obesity in rodents and humans are associated with high circulating leptin levels; the resistance to leptin that characterizes these states has not yet been explained. Potential sites for leptin resistance include the blood-brain-barrier transport system and the leptin signaling mechanism in leptin-responsive neurons in the hypothalamus. Rodents with obesity induced by high-fat diet (diet-induced obesity, or DIO) become hyperleptinemic, and food intake and body weight are resistant to the effects of exogenous leptin administered peripherally.

Diabetes mellitus induces a variety of metabolic abnormalities because of insufficient insulin action. Of these, abnormalities in glucose metabolism are the most specific and are manifested clinically as hyperglycemia after glucose ingestion. In type 2 diabetes mellitus, which affects the majority of patients with diabetes mellitus, the factors involved in the pathogenesis and the progression of the disease are insufficient insulin secretion and decreased insulin sensitivity (insulin resistance). The relationship between insufficient insulin secretion and diabetes mellitus was underscored by the discovery of the causative gene for maturity onset diabetes of the young, and abnormalities in insulin secretion are considered to be particularly important. Prevention of the progression of pancreatic β-cell dysfunction in subjects with diabetes mellitus should be a key in the long-term management of this disease.

Diabetes mellitus is a major risk factor of HF and coronary artery disease (Fuller, et al., *Br Med J* (*Clin Res Ed*) 1983, 287(6396): 867-870). Diabetes mellitus induces a variety of metabolic abnormalities because of insufficient insulin action. Of these, abnormalities in glucose metabolism are the most specific and are manifested clinically as hyperglycemia after glucose ingestion. In type 2 diabetes mellitus, the factors involved in the pathogenesis and the progression of the disease are insufficient insulin secretion and decreased insulin sensitivity (insulin resistance).

Exercise intolerance is a common feature in patients with HF and affects their quality of life, thus becoming an important target for therapies. In addition, exercise training has been widely understood as effective treatment for HF (Baladay, *Ann Med,* 1998, 30 Suppl 1:61-65; Massie, *Am J Med.,* 1988, 84(3A): 75-82). However, paradoxically, this training is prevented by exercise intolerance arising from HF. Therefore, increasing exercise capacity is favorable for HF patients in terms of not only improving prognosis and quality of life but also providing effective therapy for HF.

Hyperglycemia and hyperlipidemia have been shown to affect the mechanism of insulin secretion. Impaired glucose-mediated insulin secretion from pancreatic β-cells leads to insulin insufficiency and thus hyperglycemia and lipid metabolism abnormalities. The hyperglycemic state leads to overworking of pancreatic β-cells and a decreased ability to secrete insulin. C57BL/KsJ db/db mice that have the db mutation exhibit a severe insulin resistance and impaired insulin secretion. They are widely used as experimental models of obese type 2 diabetes mellitus. Briefly, after birth these mice have unrepressed eating behavior, become obese, and develop severe insulin resistance associated with hyperinsulinemia, hyperglycemia, and hypertriglyceridemia, so that by 3-6 months after birth, the pancreatic islet β-cells reduce their mass, resulting in severe insufficiency of insulin secretion.

Obesity, diabetes and exercise are inextricably linked such that an agent that improves exercise tolerance or prevents obesity or the development of diabetes will likely have a therapeutic role in all three conditions. Obesity, a global epidemic, promotes diabetes and is a major cardiovascular risk factor, resulting in reduced life expectancy. Finding a novel therapeutic approach would be a major advance. Recently, a novel, genetically engineered mouse model, where the adenylyl cyclase (AC) type 5 isoform is knocked out (AC5 KO) was reported. AC5 inactivation resulted in increased longevity and was protective against stress. Furthermore, the AC5 KO mice ate more than WT mice, but weighed less, suggesting that AC5 inhibition could be a novel approach to weight loss. The AC5 KO mouse also demonstrates enhanced exercise tolerance. A pharmacological AC5 inhibitor protects against cardiovascular stress.

SUMMARY OF THE INVENTION

The invention provides compositions and methods for treating obesity, atherosclerosis and diabetes mellitus as well as related diseases by administering to a patient an effective amount an AC5 inhibitor.

In a first aspect, the invention provides a method of treating obesity comprising administering a pharmaceutically effective amount of at least one compound capable of inhibiting AC5 to a patient. The compound capable of inhibiting AC5 may be administered singly or in combination with another agent, such as, for instance a β-blocker. In some embodiments, the AC5 inhibiting compound is 9-β-D-arabinofuranosyladenine (AraAde). The compounds may be administered in an amount of about 1 to about 200 mg/kg/day, about 1 to about 100 mg/kg/day, about 10 to about 80 mg/kg/day, about 12 to about 40 mg/kg/day or about 15 to about 25 mg/kg/day. In some embodiments, the compound is administered orally. The obesity may be characterized, for instance, by the patient demonstrating a body weight that is 10%, 20%, 30%, 40%, 50%, 60%, 70%, 80%, 90%, 100% or more greater than the recommended body weight for a particular gender and height as recommended by the American Medical Association or the National Board of Internal Medicine, for instance. The compound capable of inhibiting AC5 may be administered alone or in conjunction with one or more other active agents.

In a second aspect, the invention provides a method of inhibiting weight gain comprising administering a pharmaceutically effective amount of at least one compound capable of inhibiting AC5 to a patient. The compound capable of inhibiting AC5 may be administered singly or in combination with another agent, such as, for instance a β-blocker. In some embodiments, the AC5 inhibiting compound is 9-β-D-arabinofuranosyladenine (AraAde). The compounds may be administered in an amount of about 1 to about 200 mg/kg/day, about 1 to about 100 mg/kg/day, about 10 to about 80 mg/kg/day, about 12 to about 40 mg/kg/day or about 15 to about 25 mg/kg/day. In some embodiments, the compound is administered orally. The reduction in weight gain may be measured as, for instance 10%, 20%, 30%, 40%, 50%, 60%, 70%, 80%, 90%, 100% or more reduction in weight gain than that experienced in patients not undergoing treatment. The compound capable of inhibiting AC5 may be administered alone or in conjunction with one or more other active agents.

In a third aspect, the invention provides a method of treating diabetes mellitus comprising administering a pharmaceutically effective amount of at least one compound capable of inhibiting AC5 to a patient. Also, this second aspect features methods of reducing the complications from diabetes mellitus including, for instance, atherosclerosis, peripheral neuropathy, heart attack, impaired vision, etc. The compound capable of inhibiting AC5 may be administered singly or in combination with another agent. In some embodiments, the AC5 inhibiting compound is 9-β-D-arabinofuranosyladenine (AraAde). The treatment may result in, for instance, elimination of the need to administer insulin treatment to a patient or a reduction in the amount of insulin that must be administered to a patient in order to maintain blood glucose levels within a normal or acceptable range. The reduction in amount of insulin required may be, for instance, a 10%, 25%, 33%, 50% or 75% or more reduction. The compounds may be administered in an amount of about 1 to about 100 mg/kg/day, about 10 to about 40 mg/kg/day or about 15 to about 25 mg/kg/day. In some embodiments, the compound is administered orally.

In a fourth aspect, the invention provides a method of inhibiting atherosclerosis comprising administering a pharmaceutically effective amount of at least one compound capable of inhibiting AC5 to a patient. The method may feature a 10%, 20%, 30%, 40%, 50%, 60%, 70%, 80%, 90%, 100% or more reduction in the rate at which atherosclerotic plaques form, or it may even result in a reduction of 10%, 20%, 30%, 40%, 50%, 60%, 70%, 80%, 90%, 100% or more of the atherosclerotic plaques already existing in a patient. The compound capable of inhibiting AC5 may be administered singly or in combination with another agent. In some embodiments, the AC5 inhibiting compound is 9-β-D-arabinofuranosyladenine (AraAde). The compounds may be administered in an amount of about 1 to about 100 mg/kg/day, about 10 to about 40 mg/kg/day or about 15 to about 25 mg/kg/day. In some embodiments, the compound is administered orally.

Since obesity, weight gain, atherosclerosis and diabetes mellitus both contribute to and result from other related disorders and conditions, included within these first, second, third and fourth aspects of the invention are methods of improving cardiac function, including, for instance, lowering LVEDP, increasing LV dP/dt and increasing LVEF, methods of lowering or reducing myocardial apoptosis, methods of increasing exercise capacity, methods of reducing insulin resistance, and methods of reducing cardiac fibrosis. Additionally, also included within these aspects of the invention are methods of lowering fasting blood glucose, methods of lowering the plasma insulin concentration or level, methods of lowering the plasma triglyceride concentration or level, methods of improving glucose tolerance, and methods of lowering the ratio of body weight to food intake. All of these included methods once again comprising administering a pharmaceutically effective amount of at least one compound capable of inhibiting AC5 to a patient. The methods may feature a 10%, 20%, 30%, 40%, 50%, 60%, 70%, 80%, 90%, 100% or more reduction or increase in the respective value measured, e.g. plasma glucoce, insulin or triglyceride concentration. The compound capable of inhibiting AC5 may be administered singly or in combination with another agent. In some embodiments, the AC5 inhibiting compound is 9-β-D-arabinofuranosyladenine (AraAde). The compounds may be administered in an amount of about 1 to about 100 mg/kg/day, about 10 to about 40 mg/kg/day or about 15 to about 25 mg/kg/day. In some embodiments, the compound is administered orally.

In a fifth aspect, the invention provides a composition effective for treating one or more of obesity, diabetes mellitus and atherosclerosis containing at least one compound capable of inhibiting AC5. The composition may contain one or more other therapeutic compounds. In some embodiments, the AC5 inhibiting compound is 9-β-D-arabinofuranosyladenine (AraAde). The composition may be formulated to be administered in an amount of about 1 to about 100 mg/kg/day, about 10 to about 40 mg/kg/day or about 15 to about 25 mg/kg/day. In some embodiments, the composition is formulated to be administered orally.

DETAILED DESCRIPTION OF THE INVENTION

Definitions

Figure 1:
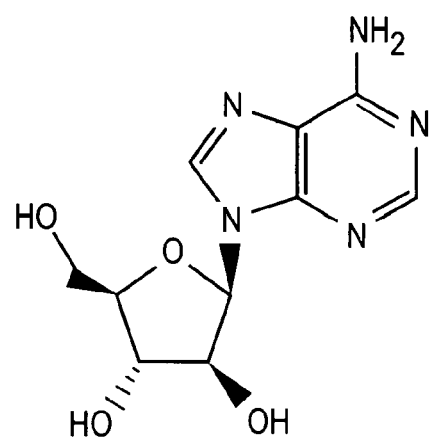
FIG. 1 provides the chemical structure of AraAde.

"Obesity" refers to a body weight that is greater than that recommended by prevailing medical authorities, e.g. the American Medical Association and the National Board of Internal Medicine, and literature for a particular gender and height. It may refer to a body weight that is 10%, 20%, 30%, 40%, 50%, 60%, 75%, 90%, 100%, 200% or more greater than the recommended normal body weight.

"Diabetes Mellitus" refers to a disorder characterized by abnormal insulin production, abnormal response to insulin, or production of insulin lacking sufficient biological activity, resulting in an inability to consistently maintain blood glucose levels within a normally accepted range.

"Atherosclerosis" refers to a pathology characterized by accumulation of fatty plaque along artery walls or in the arteries of a patient.

"Inhibitor of AC5" includes but is not limited to, any suitable molecule, compound, protein or fragment thereof, nucleic acid, formulation or substance that can regulate AC5 activity in such a way that AC5 activity is decreased. The inhibitor can include, but is not limited to, the specifically identified ribose-substituted P-site ligands such THFA 9-(tetrahydro-2-furyl) adenine and CPA 9-(cyclopentyl) adenine or 2-amino-7-(2-furanyl)-7,8-dihydro-5(6H)-quinazoline (NKY80) and 9-β-9-β-arabinofuranosyladenine (AraAde).

"Mammal" refers to any animal classified as a mammal, including humans, domestic and farm animals, and zoo, sports, and pet companion animals, and other domesticated animal such as, but not limited to, cattle, sheep, ferrets, swine, horses, poultry, rabbits, goats, dogs, cats, and the like.

"Patient" refers to a mammal, preferably a human, in need of treatment for a condition, disorder or disease.

Pharmaceutically acceptable salts include salts of compounds derived from the combination of a compound and an organic or inorganic acid. These compounds are useful in both free base and salt form. In practice, the use of the salt form amounts to use of the base form; both acid and base addition salts are within the scope of the present invention.

Pharmaceutically acceptable acid addition salt refers to salts retaining the biological effectiveness and properties of the free bases and which are not biologically or otherwise undesirable, formed with inorganic acids such as hydrochloric acid, hydrobromic acid, sulfuric acid, nitric acid, phosphoric acid and the like, and organic acids such as acetic acid, propionic acid, glycolic acid, pyruvic acid, oxalic acid, maleic acid, malonic acid, succinic acid, fumaric acid, tartaric acid, citric acid, benzoic acid, cinnamic acid, mandelic acid, methanesulfonic acid, ethanesulfonic acid, p-toluenesulfonic acid, salicyclic acid and the like.

Pharmaceutically acceptable base addition salts include those derived from inorganic bases such as sodium, potassium, lithium, ammonium, calcium, magnesium, iron, zinc, copper, manganese, aluminum salts and the like. Particularly preferred are the ammonium, potassium, sodium, calcium and magnesium salts. Salts derived from pharmaceutically acceptable organic nontoxic bases include salts of primary, secondary, and tertiary amines, substituted amines including naturally occurring substituted amines, cyclic amines and basic ion exchange resins, such as isopropylamine, trimethylamine, diethylamine, triethylamine, tripropylamine, ethanolamine, 2-diethylaminoethanol, trimethamine, dicyclohexylamine, lysine, arginine, histidine, caffeine, procaine, hydrabamine, choline, betaine, ethylenediamine, glucosamine, methylglucamine, theobromine, purines, piperizine, piperidine, N-ethylpiperidine, polyamine resins and the like. Particularly preferred organic nontoxic bases are isopropylamine, diethylamine, ethanolamine, trimethamine, dicyclohexylamine, choline, and caffeine.

"Prodrug" refers to a pharmacologically inactive derivative of a parent drug molecule that requires biotransformation, either spontaneous or enzymatic, within the organism to release the active drug. Prodrugs are variations or derivatives of the compounds of this invention which have groups cleavable under metabolic conditions. Prodrugs become the compounds of the invention which are pharmaceutically active in vivo, when they undergo solvolysis under physiological conditions or undergo enzymatic degradation.

"Therapeutically effective dose" refers to the dose that produces the biological effects for which it is administered.

"Treat" and "treatment" refers to both therapeutic methods and prophylactic or preventative measures, wherein the object is to prevent or slow down (lessen) an undesired physiological condition, disorder or disease or to obtain beneficial or desired clinical results. For purposes of this invention, beneficial or desired clinical results include, but are not limited to, alleviation of symptoms; reduction in the extent of a condition, disorder or disease; stabilization of (i.e. not worsening) a state or condition, disorder or disease; delay or slowing of a condition, disorder, or disease progression; amelioration of the condition, disorder or disease state; remission (whether partial or total), whether detectable or undetectable; or enhancement or improvement of a condition, disorder or disease. Treatment may also include eliciting a cellular response that is clinically significant, without excessive side effects. Treatment may also include prolonging survival as compared to expected survival without treatment. Since obesity, weight gain, atherosclerosis and diabetes mellitus both contribute to and result from other related disorders and conditions, treat and treatment may, for this invention, include improving cardiac function, including, for instance, lowering LVEDP, increasing LV dP/dt and increasing LVEF, lowering or reducing myocardial apoptosis, and reducing cardiac fibrosis. Additionally, "treat" and "treatment" may include lowering fasting blood glucose, lowering the plasma insulin concentration or level, lowering the plasma triglyceride concentration or level, improving glucose tolerance, and lowering the ratio of body weight to food intake.

Classic inhibitors of AC include adenosine analogs or P-site inhibitors, and MDL12330A, a non-nucleic acid inhibitor. Classic P-site inhibitors with phosphate at the 3' position such as 2'-d-3'-AMP and 3'-AMP potently inhibited AC catalytic activity. 2'-d-3'-AMP potently inhibited AC5 and AC3 while to a lesser degree AC2; the selectivity ratio was 27 between AC5 and AC2.

The $IC_{50}$ values for each isoform were calculated to be 0.82 µM for AC5, 2.8 µM for AC3 and 22.4 µM for AC2. In contrast, ribose-substituted P-site inhibitors, such as THFA and CPA, potently inhibited AC5 while they inhibited AC2 and AC3 only to a modest degree in the presence of Gs-α/GTPαS/forskolin. The $IC_{50}$ value was calculated as 2.2 µM for AC5, 101 µM for AC3 and 285 µM for AC2. It was previously noted that AC2 was less sensitive to THFA than the other isoforms, giving a selectivity ratio of 1.8 when compared between AC6 and AC2. Inventors found that the selectivity ratio was even greater (130) between AC5 and AC2.

The present invention demonstrates that 9-β-arabinofuranosyladenine (AraAde), now used for treating viral infections, shows potent and selective AC5 inhibition (*Physicians' Desk Reference* 2006. Montvale, N.J.: Thomson PDR; 2006; Kleymann G. *Expert Opin Investig Drugs.* 2003;12(2):165-183; Whitley *Ann Pharmacother.* 1996; 30(9):967-971; Whitley et al., *Antimicrob Agents Chemother.* November 1980; 18(5):709-715).

Amantadine, which was originally developed as a drug for treating Parkinson's disease, is now widely used for treating virus infection such as influenza or hepatitis C virus (Jefferson et al., *Cochrane Database Syst Rev.* 2006(2):CD001169; Wohnsland et al., *Clin. Microbiol. Rev.* 2007;20(1):23-38).

TABLE 1

$IC_{50}$ and selectivity ratios of AC inhibitors in recombinant AC proteins. 2'5'-dd-Ado and AraAde are potent, selective AC5 inhibitors. Selectivity ratio for AC5 is the ratio of $IC_{50}$ for AC5 to that for AC2 or AC3, which indicates the selectivity for AC5 among other subtypes.

|  |  | 2'5'-dd-Ado | Ara-Ade | PMC-6 |
|---|---|---|---|---|
| $IC_{50}$ | AC2 | 2382 | 7202 | 65.3 |
|  | AC3 | 253 | 375 | 11.1 |
|  | AC5 | 1.6 | 9.8 | 0.32 |
| Selectivity | AC5/AC2 | 0.00067 | 0.0014 | 0.0049 |
| ratio for AC5 | AC5/AC3 | 0.0063 | 0.027 | 0.029 |

Drugs with Adenosine-like Structure have an AC5 Inhibitory Effect

To find more potent AC5 inhibitors than AraAde, drugs with the adenosine-like structure, which is required for binding to and inhibition of AC, were tested. Several approved and experimental drugs that show AC5 inhibition were found. Since the catalytic site of AC is in the intracellular domain, the plasma membrane permeability of these drugs using H9C2, a cardiac myoblast cell line was examined. These inhibitors also show AC inhibition in H9C2, suggesting that these drugs exert the AC inhibitory effects when administered to intact cells. Among these inhibitors, fludarabine, an anti-leukemia drug, showed more potent inhibition of AC5 and cAMP accumulation than AraAde; however, fludarabine is known to have severe adverse effects including bone marrow suppression which occur in roughly half of administered patients.

Adenylyl Cyclase Type 5 (AC5) Knockout (KO) Mice

Figure 3:
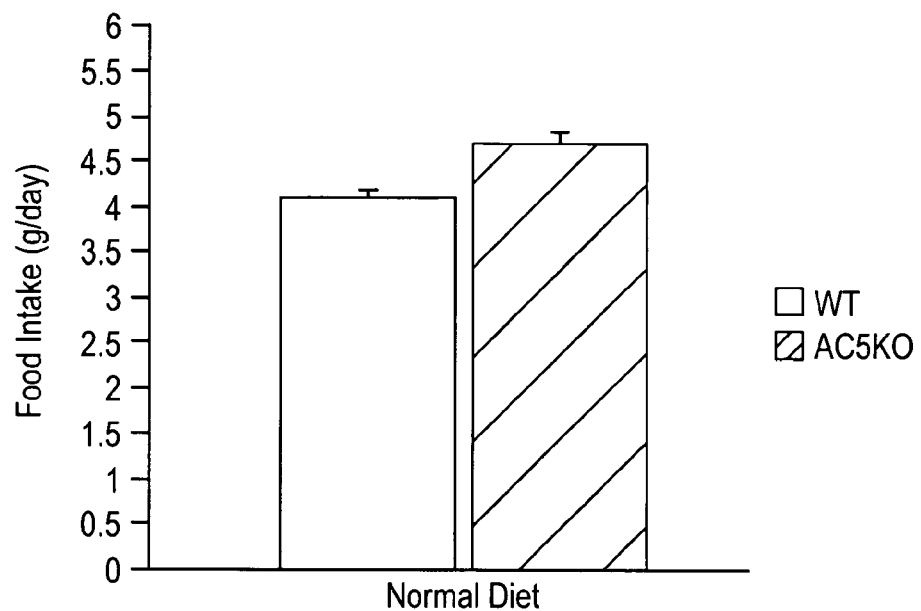
FIG. 3 demonstrates food intake in WT and AC5 KO mice. AC5 KO mice ingested more food than WT mice when fed a normal diet (ND; 90 kcal/week). Even though they ate more, the AC5 KO mice still weighed less than WT mice (FIGS. 3 and 4). *$p<0.05$.
Figure 4:
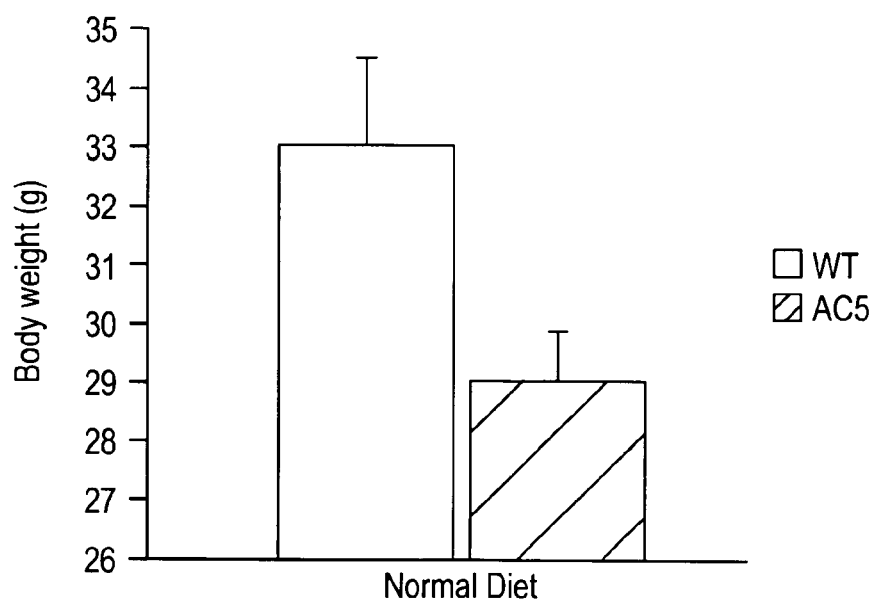
FIG. 4 demonstrates that AC5 KO mice weigh less that WT mice. When fed a normal diet (ND; 90 kcal/week), AC5 KO mice ate more but weighed less. *$p<0.05$.

Recently, a novel, genetically engineered mouse model, in which type 5 adenylyl cyclase (AC5) is knocked out (AC5 KO) was reported. These mice exhibit increased longevity and protection against stress, e.g. resistance to development of heart failure (HF) following chronic pressure overload and chronic catecholamine stimulation. These mice eat more than wild-type (WT), but weigh less (FIGS. 3 and 4). This, in combination with preliminary data showing enhanced exercise tolerance and sensitivity to caloric restriction (CR) (see FIGS. 4 and 8), demonstrates that inhibition of AC5 is a novel approach for weight loss therapy. Since it is not feasible to knock out this gene in patients, a pharmacological AC5 inhibitor, Adenine 9-β-D-arabinofuranoside (AraAde), which represents the paradigm for this therapeutic approach, was developed.

AC Plays a Major Role in Energy Restoration and Usage

AC is a 12-transmembrane protein that catalyzes the conversion of ATP to cAMP upon the stimulation of various G-protein coupled receptors such as β-adrenergic receptors. Nine mammalian AC subtypes have been identified. Each subtype shows distinct tissue distribution, and biological and pharmacological properties. Stimulation of G protein-coupled receptors induces binding of the stimulatory Gα subunit (Gsα) to AC, and enhances its catalytic activity to convert ATP into cAMP. cAMP is an important second messenger and regulates multiple cellular functions including gluconeogenesis through its target protein, protein kinase A. Also, glucagon activates AC, which leads to gluconeogenesis. Data shows that AC5 KO mice eat more, weigh less and have reduced glucose with CR. Accordingly, AC5 plays a large role in controlling the abnormalities in glucose metabolism that accompany obesity and diabetes.

The major sites for regulation of glycolysis and gluconeogenesis are the phosphofructokinase-1 (PFK-1) and fructose-1,6-bisphosphatase (F-1,6-BPase) catalyzed reactions. PFK-2 is the kinase activity and F-2,6-BPase is the phosphatase activity of the bi-functional regulatory enzyme, phosphofructokinase-2/fructose-2,6-bisphosphatase. Protein kinase (PKA) is cAMP-dependent protein kinase which phosphorylates PFK-2/F-2,6-BPase turning on the phosphatase activity. The interconversion of the bifunctional enzyme is catalyzed by cAMP-dependent PKA, which in turn is regulated by circulating peptide hormones. When blood glucose levels drop, pancreatic insulin production falls, glucagon secretion is stimulated, and circulating glucagon is highly increased. Hormones such as glucagon bind to plasma membrane receptors on liver cells, activating membrane-localized adenylyl cyclase leading to an increase in the conversion of ATP to cAMP. cAMP binds to the regulatory subunits of PKA, leading to release and activation of the catalytic subunits. PKA phosphorylates numerous enzymes, including the bifunctional PFK-2/F-2,6-BPase. Under these conditions the liver stops consuming glucose and becomes metabolically gluconeogenic, producing glucose to reestablish normal glycemia. Thus AC5 plays a large role in controlling the abnormalities in glucose metabolism that accompany obesity and diabetes.

Development of AC5 Inhibitors

Classic inhibitors of AC, known as P-site inhibitors, have been studied since the 1970's. It was first thought that there was an adenosine-reactive site within the intracellular domain of AC, the "P" site, which inhibits the catalytic activity of AC. In spite of the fact that the chemical structure of P-site inhibitors was similar to that of the substrate ATP, P-site inhibitors showed un- or non-competitive inhibition with respect to ATP. It is desirable to develop P-site inhibitors with enhanced AC isoform selectivity. Several groups have developed such experimental systems using the baculovirus-based recombinant AC overexpression system and have found selective P-site inhibitors for AC5, including AraAde.

In addition to these AC5 inhibitors, existing drugs which have an adenosine-like structure were screened, and new AC5 inhibitors were found. Among them, adenine 9-β-D-arabinofuranoside (AraAde), an anti-virus drug, shows potent AC5 inhibition. AraAde is an analog of adenosine with the D-ribose sugar, replaced with D-arabinose, and is a stereoisomer of adenosine. AraAde has inhibitory properties for viruses including herpesvirus, poxviruses, rhabdoviruses, hepadnaviruses and some RNA tumour viruses (Iwamoto, et al., *J Biol Chem*, 2003, 278(19): 16936-16940). AraAde is now used in the clinic as an ophthalmic ointment for keratoconjuctivitis caused by herpes virus, and many of the previous uses in IV have been superseded by acyclovir because of acyclovir's higher selectivity, lower inhibitory concentration and higher potency. In addition, AraAde inhibited myocardial apoptosis in vitro and in vivo, and attenuated LV dysfunction in HF mice induced by excessive chronic β-AR stimulation, indicating the possibility of the use of AraAde in clinics, as a heart failure (HF) drug. In addition, AraAde was reported to have little blood-brain barrier-permeability. AraAde does not induce bradykinesia and impaired locomotor activity which were observed in AC5 KO. This indicates that AraAde does not affect brain function.

Similarities Between AC5 Inhibition and Caloric Restriction (CR)

Several lines of evidence point to abnormalities in metabolism with models of enhanced longevity. The most widely studied and best-accepted model of longevity, CR, by definition will affect metabolism, i.e., reduced caloric intake results in less energy metabolism from external sources. In that model and many genetic models of enhanced longevity there is a lower metabolic rate, decreased body temperature, and reduced visceral fat and body mass. The precise metabolic alterations in these models, particularly at the level of intermediary metabolism, have not been elucidated entirely. Importantly, it is know that both models exhibit enhanced longevity, stress resistance, decreased body weight, decreased growth hormone and decreased responsiveness to sympathetic stimulation.

Recently, a genetically engineered mouse model, where adenylyl cyclase (AC) type 5 isoform is knocked out (AC5 KO) was reported. AC5 inactivation resulted in increased longevity and was protected against stress. In view of the fact that AC5 KO mice eat more and weigh less and the similarities in this model of longevity and stress resistance with CR, an important component of the mechanism of the beneficial effects of CR, and AC5 KO, is an alteration in intermediary metabolism. Apart from systemic changes in metabolism and circulating fuels for energy production, probably the intrinsic metabolic adaptations in the myocardium for both AC5 KO and CR models during aging and/or pressure overload are similar in minimizing the inefficiency of the altered intermediary metabolic pathways that develop in response to aging and pressure overload hypertrophy in hearts of WT. These inefficiencies include reduced long chain fatty acid (LCFA) oxidation, mismatch between accelerated glycolytic flux and reduced oxidation of glucose end-products.

This approach provides the basis for new anti-obesity and anti-diabetes therapy. Inhibition of AC5 in mice protects against obesity. Inhibition of AC5 will ameliorate obesity in mice fed a high fat diet, and inhibition of AC5 will ameliorate the development of insulin resistance and diabetes, and will improve exercise tolerance in the mice.

AC5 KO Mice Live 30% Longer Than WT Mice

Figure 2:
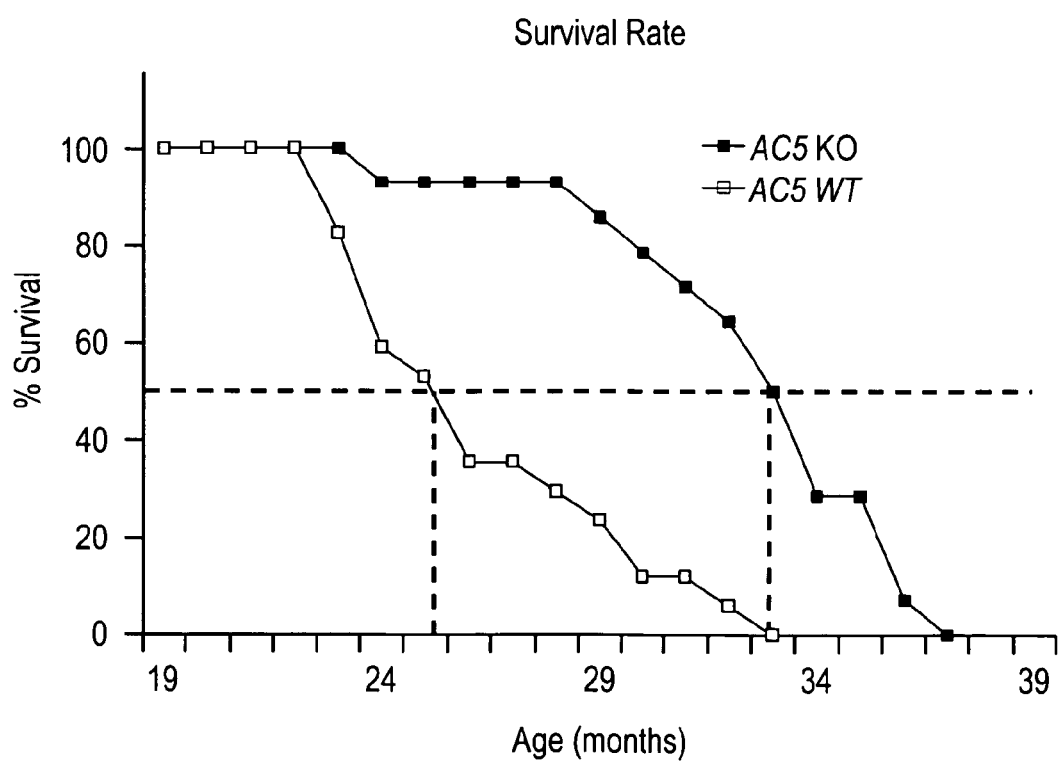
FIG. 2 demonstrates extended life span in AC5KO mice. The KaplanMeier survival curve shows significantly increased survival, $p<0.01$, of AC5 KO mice compared to their wild type (WT) littermates studied anterospectively from birth to death. The dotted line indicates the time of 50% survival. Roughly 50% of WT mice died by 25 months. At 33 months, all WT mice had died, whereas 50% of AC5 KO mice were still alive. These differences are significant, $p<0.01$. The maximum survival was also significantly different, $p<0.02$, by the Chi square test.

It is well recognized that longevity is related to stress resistance. AC5 KO mice live approximately one-third longer than WT (Yan, et al., *Cell*, 2007, 130(2): 247-258) (FIG. 2). In addition, AC5 KO mice on average weighed less than age-matched WT mice.

AC5 KO Mice Ingest More Food but Weigh Less Than WT MICE

Figure 5:
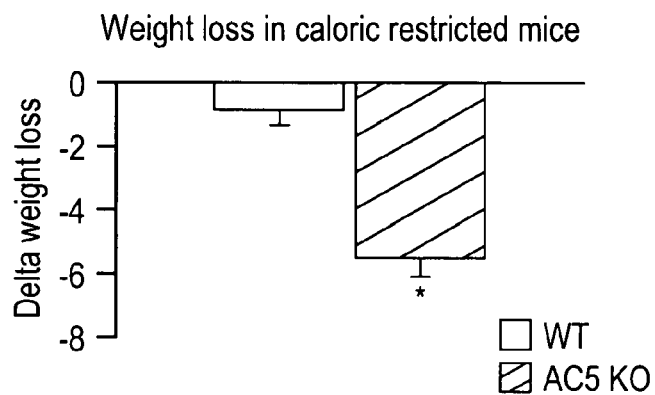
FIG. 5 demonstrates the change in weight loss in WT and AC5 KO mice after 2 weeks of caloric restriction (CR). At the time of sacrifice a clear decrease in the amount of white adipose tissue in AC5 KO mice compared with wild type controls. *$p<0.05$ was noted.

Normal diet (ND), consisting of 90 kcal/week of chemically defined control diet (AIN-93M, Diet No. F05312, Bioserv, Frenchtown, N.J.), provides approximately 10% fewer calories than normally are assumed to be required by a typical mouse. Under these conditions, AC5 KO mice, although weighing less, consumed more food than WT (FIG. 3). FIGS. 4 and 5 show that body weight of AC5 KO mice is lower compared to WT under both caloric conditions (CR and normal diet, ND).

Effects of Caloric Restriction (CR) are More Severe in AC5 KO

Figure 6:
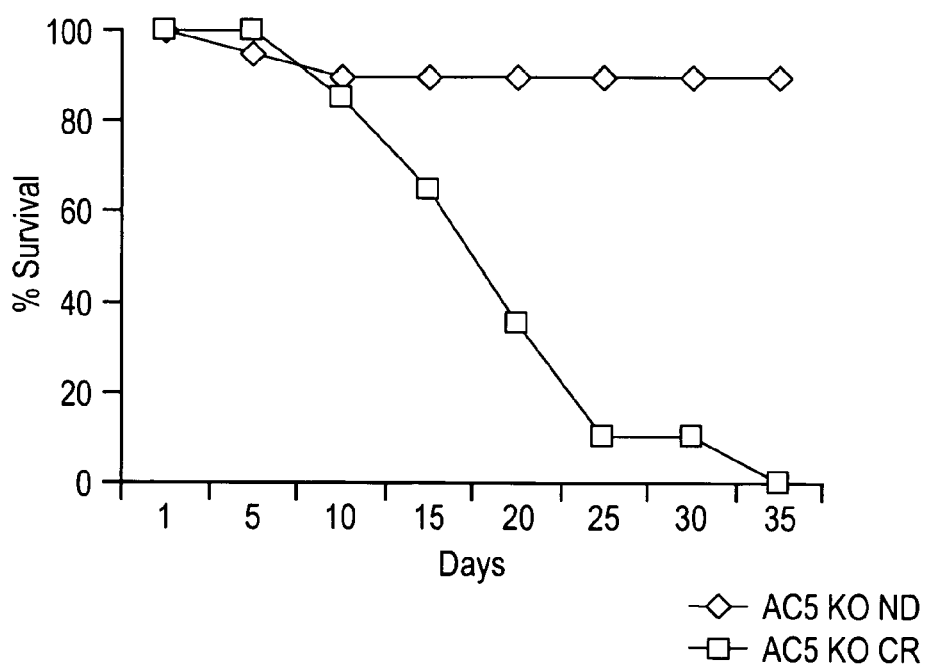
FIG. 6 demonstrates survival of AC5KO mice under CR or normal diet.

Since both CR and AC5 deletion result in increased longevity it is surprising to find that the survival rate of AC5 KO mice under CR conditions is lower than that of AC5 KO under ND (FIG. 6). No WT mice died under either CR or ND conditions (data not shown).

AC5 KO Mice Have Possible Metabolic Alteration

Figure 7:
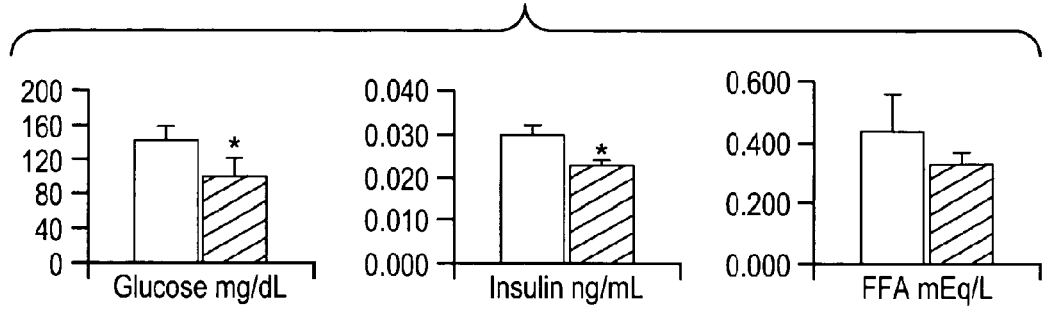
FIG. 7 demonstrates the effects of CR on blood levels of glucose, insulin and free fatty acids (FFA) in WT and AC5 KO mice.

Blood glucose, insulin and free fatty acid levels were measured in mice under different feeding conditions (FIG. 7). WT and AC5 KO mice fed a normal diet displayed similar blood glucose levels (data not shown), however, under CR, glucose and insulin levels are lower in AC5 KO mice and free fatty acids are not significantly different. These results suggest a metabolic alteration in AC5 KO animals that results in less efficient energy storage, indicating that AC5 KO unlikely develop obesity. AC5 KO mice sacrificed at the end of the experiment showed absence of fat deposits.

Tissue Distribution of AC5

Western blot analysis was carried out using membrane proteins prepared from various pig tissues. AC5 protein was found to be expressed in the heart, brain, lung, liver, stomach, kidney and skeletal muscle tissues, with the highest level of expression found in the brain (represented by the cortex and thalamus).

Exercise in AC5 KO

Figure 8:
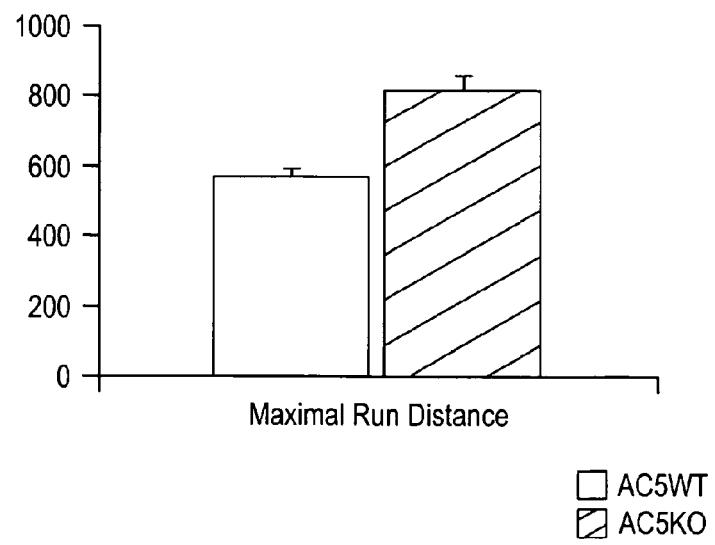
FIG. 8 demonstrates the effects of knocking out AC5 on maximal running distance. AC5 KO mice retain an enhanced maximal running distance compared to their age matched WT controls. *$p<0.05$ vs WT.

AC5 KO mice exibited an increased maximum distance run as compared to WT littermates (FIG. 8). This indicates that removal of the AC5 gene increases the exercise capability of the knockout mouse. Tsutsui et al. have reported that reactive oxygen species are increased in skeletal muscle in HF after myocardial infarction and that the reactive oxygen species originate from superoxide anions ($O_2^-$) produced by mitochondrial oxidase. $O_2^-$ reacts rapidly with nitric oxide (NO), reducing NO bioactivity and producing the oxidant peroxynitrite Kinugawa et al. showed that exercise capacity is reduced in conditions in which the superoxide anion is increased, and there is a greater increase in whole-body oxygen consumption in $SOD2^{+/-}$ compared with $SOD2^{+/+}$. Previous work has shown that AC5 KO mice exhibit an increased level of MnSOD, thus an increase in SOD could explain the increased exercise capability.

Figure 11:
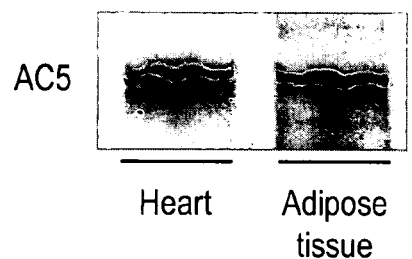
FIG. 11 demonstrates AC5 expression in adipose tissue. AC5 protein is detected by immunoblotting and is present at similar levels in the hearts and adipose tissue of WT mice.

A Novel AC5 Antibody: A critical component of the present invention requires accurate measurement of AC5 protein levels. Until this time, an adequate antibody was not available. A specific type 5 AC monoclonal antibody (mAb) was developed. This antibody demonstrates enhanced levels in AC5 Tg mice and absence of AC5 in AC5 KO mice (FIG. 11).

AC5 Expression Level is Similar in Hearts and Adipose Tissue: It is important to examine the regulation of adipose tissue by inhibition of AC5. Using the specific AC5 mAb, it was demonstrated that AC5 is present in adipose tissue (FIG. 11).

AC5 Expression Level is Elevated in Diabetic Mice

Figure 12:
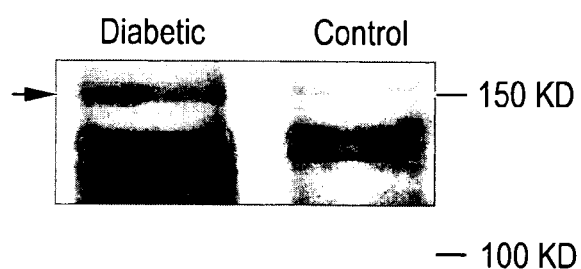
FIG. 12 demonstrates that AC5 expression is elevated in the hearts of diabetic mice. Control (C) and diabetic (D) cardiac membrane preparations were separated on an SDS PAGE blotted and probed with mouse anti-AC5 antibody. AC5 (150 KD) was found to be elevated in the cardiac tissue of diabetic FVB mice, as indicated by the arrow.

Using the specific AC5 mAb, it was demonstrated that cardiac AC5 protein expression level, as determined by western blotting (150 kD), is significantly elevated in streptozotocin induced diabetic mice when compared to matching non-diabetic mice controls (FIG. 12).

Figure 13:
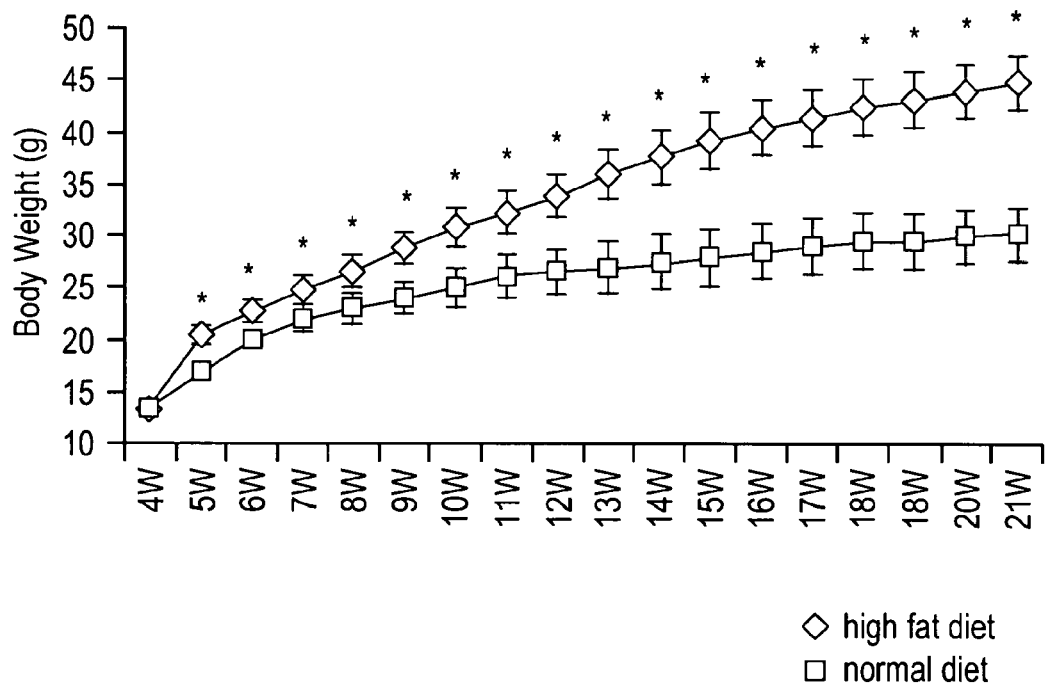
FIG. 13 demonstrates the effect of a high fat diet in WT (C57BL/6) mice. Obese diabetic mice were generated by a high-fat diet. Mice were placed at weaning (3 weeks of age) on either a high-fat diet for obese diabetic mice or a normal diet. Differences in body weight became significant at 5 weeks.* $p<0.05$ vs normal diet.
Figure 14:
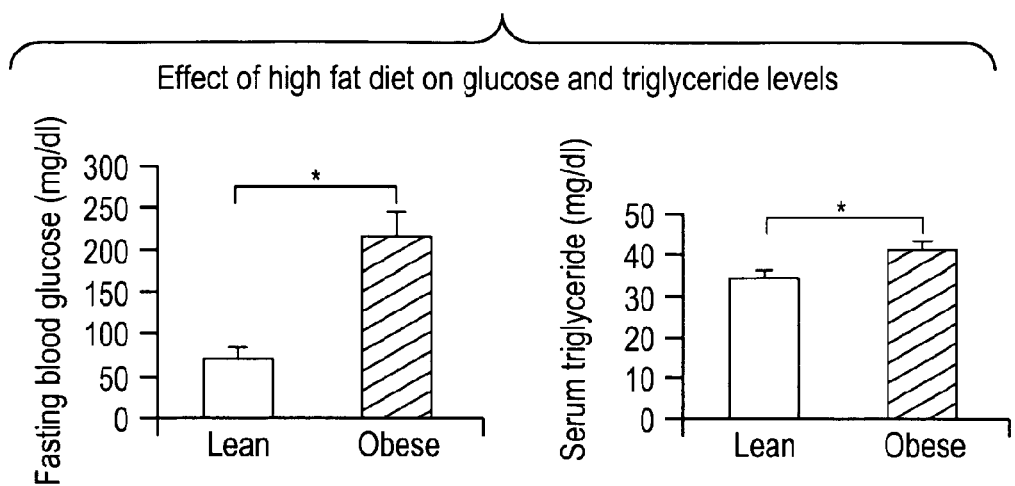
FIG. 14 demonstrates the effect of a high fat diet in WT (C57BL/6) mice. At 6 months, fasting blood glucose levels were increased approximately by three-fold (left) and serum triglycerides by 21% (right) in obese diabetic mice relative to lean normal mice.

High Fat Diet can Induce Obesity in WT C57 Mice: The effects of a high fat diet on WT C57 mice were examined to determine the amount of inducible weight gain (FIG. 13) as well as the tolerance to the diet, change in fasting glucose and serum triglyceride levels (FIG. 14).

Figure 15:
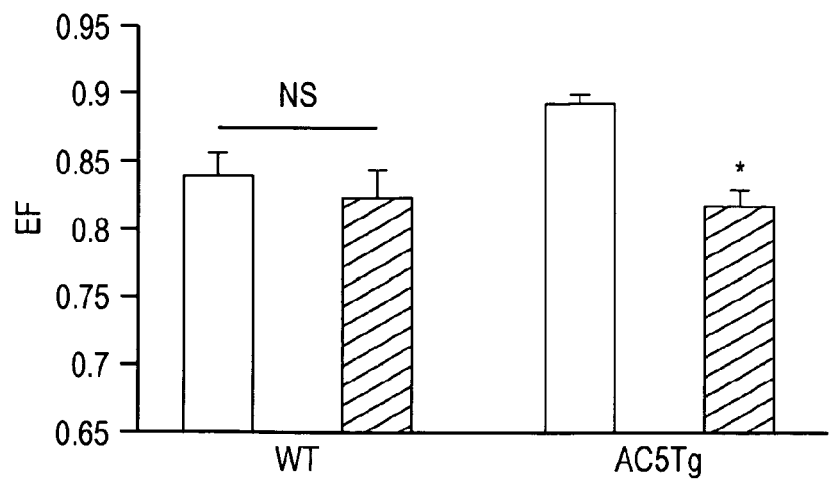
FIG. 15 demonstrates that AC5 inhibition attenuates ISO-induced increase in LVEF. LVEF was measured with an ISO challenge after chronic infusion of the AC5 inhibitor. The AC5 inhibitor decreased ISO-induced LVEF significantly in AC5 Tg mice but not in WT mice. These data showed that the AC5 inhibitor selectively suppresses AC5 in vivo. *p<0.05 vs vehicle.

Inhibition of AC5 Attenuates the Progression of Heart Failure (HF) Induced by Chronic Sympathetic Stress and Pressure Overload: AC5 KO showed protection against HF induced by chronic sympathetic stimulation. Chronic infusion of isoproterenol (ISO), a β-AR agonist, reduced LVEF in both WT and AC5 Tg, but the magnitude of the decrease was significantly greater in AC5 Tg than in WT (FIG. 15), indicating that deletion of AC5 attenuated chronic ISO-induced contractile dysfunction.

Figure 16A:
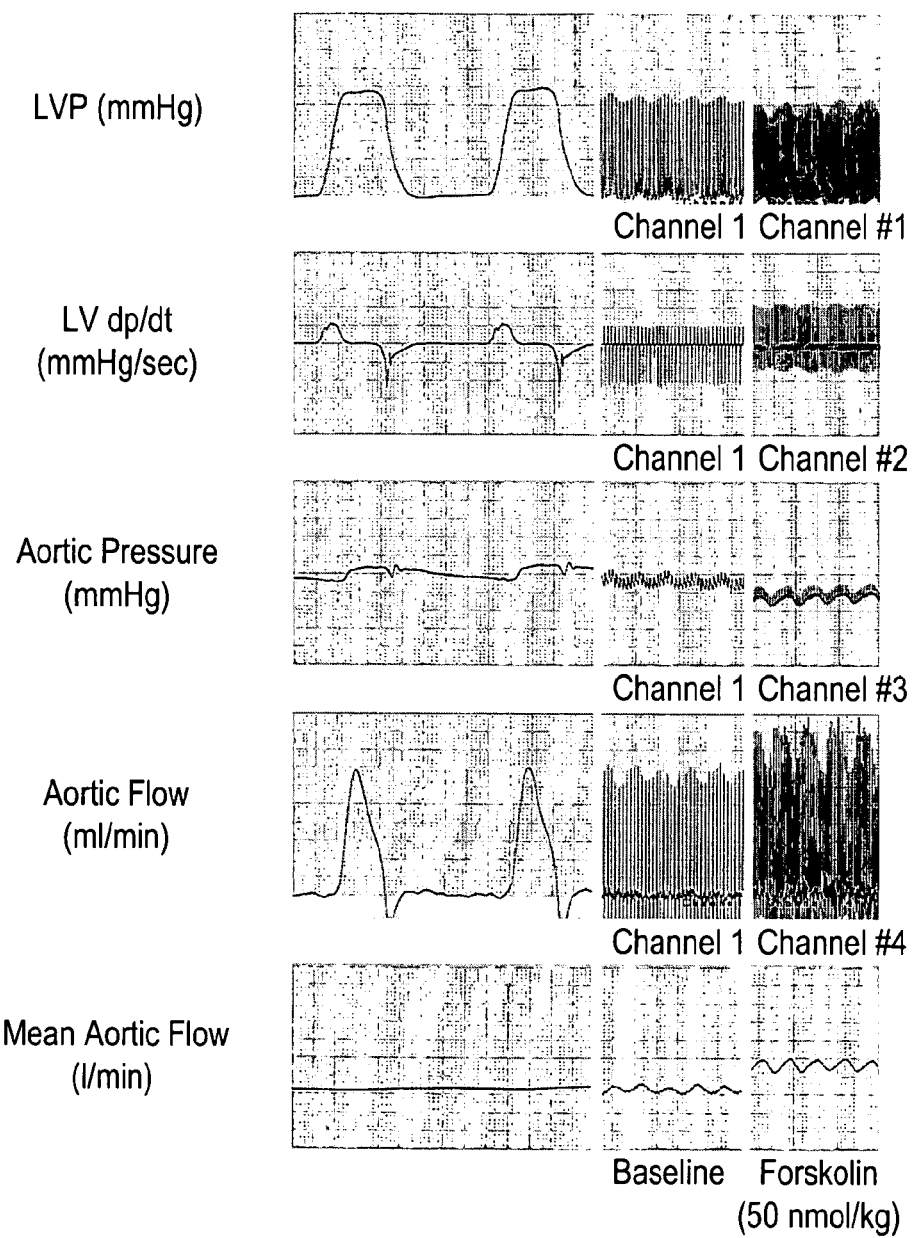
FIG. 16 demonstrates that AraAde inhibits AC activity in dogs in vivo. An adult mongrel dog (16.5 kg, male) was surgically instrumented, for measurements of LV pressure (P), LV dP/dt, aortic pressure, ascending aortic blood flow (stroke volume) and mean aortic blood flow (cardiac output). (a) The response to intravenous infusion of Forskolin (50 nmol/kg) is shown on the phasic waveforms on the left. LV dP/dt, aortic flow (stroke volume) and mean aortic flow (cardiac output) are increased. These data are consistent with those previous reports (Iwasi, et al., *Am J Physiol*, 1996, 271(4Pt2),: H1473-1482). (b and c) AraAde attenuates forskolin-induced LV dP/dt max and cardiac output. AraAde (15 mg/kg) was injected intravenously. Note that the increases in LV dP/dt and cardiac output to forskolin were diminished after AraAde.
Figure 16B:
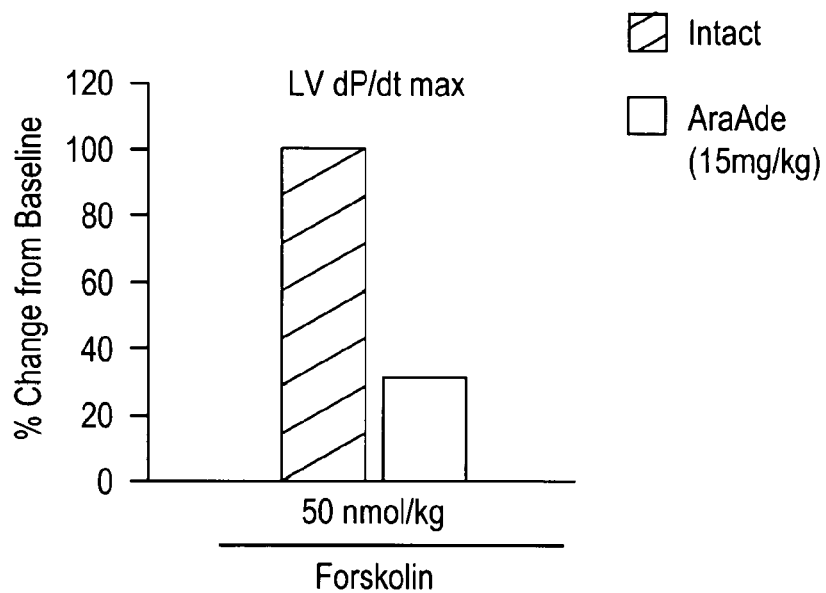
Figure 16C:
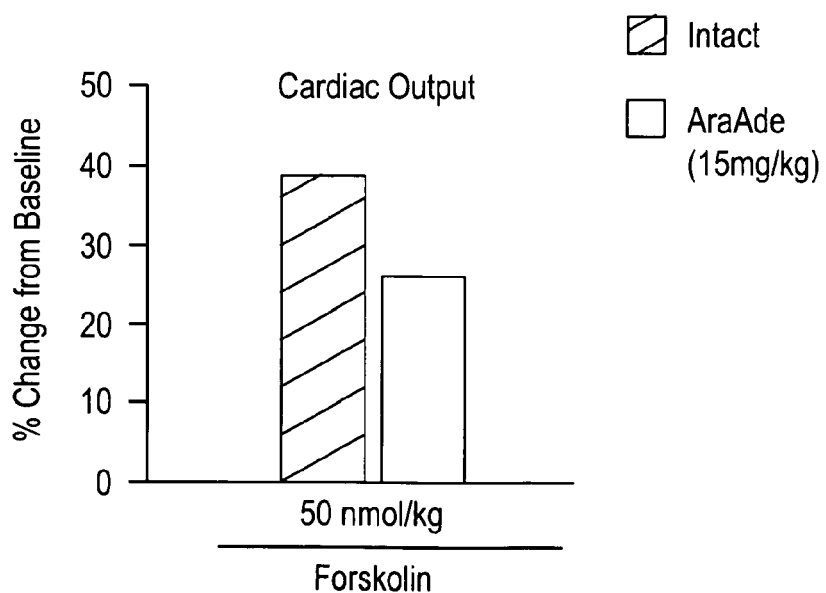

AraAde Inhibits Adenylyl Cyclase Activity in Dogs: AraAde attenuates AC activity in dogs in vivo. When AraAde was administered in dogs, forskolin-induced LV dP/dt max and cardiac output were attenuated (FIGS. 16b and c). These data are consistent with those in mice (FIG. 8a), and suggest that AraAde inhibits AC activity in the heart of dogs.

Figure 17A:
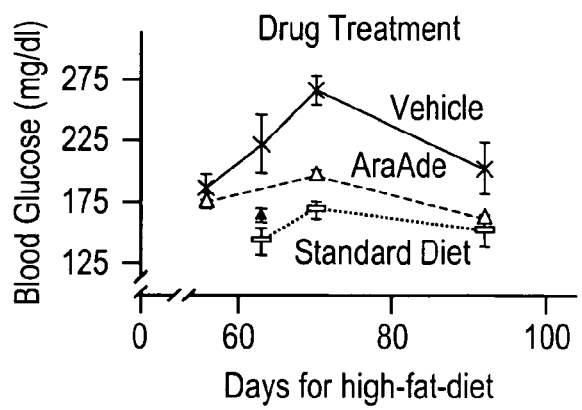
FIG. 17 (*a* and *b*) demonstrate the effect of AraAde on fasting blood glucose and plasma insulin level in high-fat-diet-fed C57BL/6 mice. a) Fasting blood glucose levels were similar at the start of therapy with AraAde, and were consistently better in the group treated with AraAde (15 mg/kg/day). Fasting glucose levels in AraAde treated mice show a trend towards the control mice on a standard diet. b) Plasma insulin levels were elevated in the vehicle treated obese diabetic mice, consistent with increased insulin resistance in this group. However, in the group treated with AraAde, the elevation in insulin was minimal compared with control animals on standard diet. This was also reflected in the insulin resistance profile. n=3 for standard diet, n=3 for vehicle and n=2 for AraAde. c) Net Ratio of Body Weight to Food intake in AraAde-treated mice. The ratio was calculated with total body weight gain and food intake during the 42 days of AraAde treatment. In AraAde-treated mice, a decreased ratio of body weight gain to food intake (high-fat-diet) was observed. The weight gain per gram of food consumed in the AraAde treated group on high fat diet was similar to that of the control group on standard diet. n=3 for standard diet, n=3 for vehicle and n=2 for AraAde.
Figure 17B:
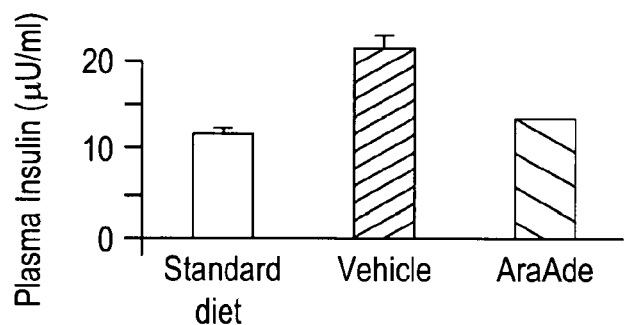
Figure 17C:
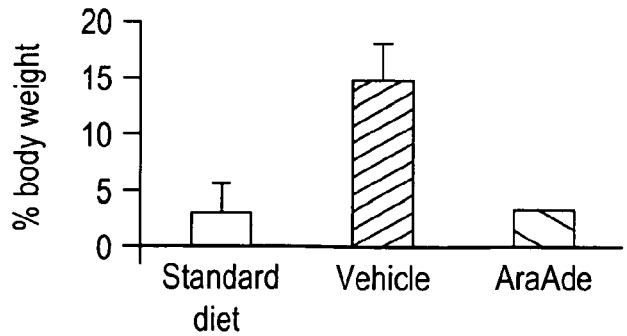

AraAde Decreases Fasting Blood Glucose, Plasma Insulin and Body Weight Gain Induced by High-Fat Diet in Mice. The effect of AraAde administration on fasting blood glucose levels and the ratio of weight gain to food intake in high-fat fed C57Bl/6 mice was examined. AraAde treated mice showed decreased fasting blood glucose (FIG. 17a) whereas plasma insulin level was unchanged (FIG. 17b). In addition, AraAde decreased the ratio of body weight gain to food intake (FIG. 17c). These data indicate that AraAde improves disorders of glucose metabolism.

Figure 18A:
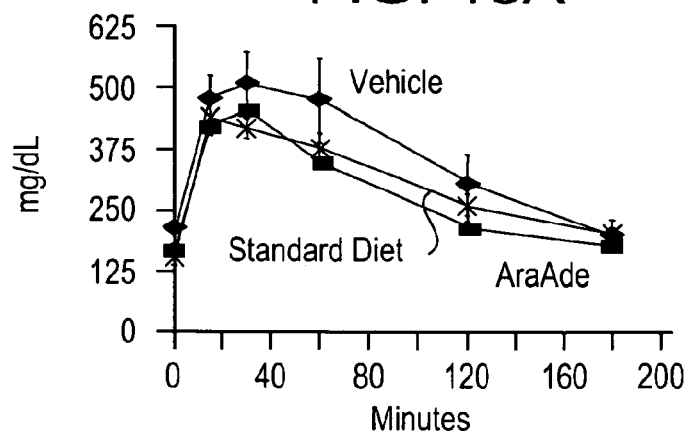
FIG. 18 demonstrates that AraAde improves glucose tolerance, insulin resistance and β-cell function. a) The glucose tolerance curve of the AraAde treated group closely parallels that of the control mice on standard diet, while the vehicle treated group showed a clearly higher glucose level at all time points and a longer recovery time to baseline. b) Insulin resistance, determined by HOMA IR, was improved in the AraAde treated group (6.38) compared to the vehicle treated group (8.38). c) The vehicle treated group was found to have an elevated relative pancreatic β-cell function, determined by HOMA β, compared to the control mice on standard diet, reflecting increased insulin secretion. This was in contrast to the relatively preserved HOMA % β in the AraAde treated group. n=3 for standard diet group, n=3 for vehicle treated group and n=2 for AraAde treated group.
Figure 18B:
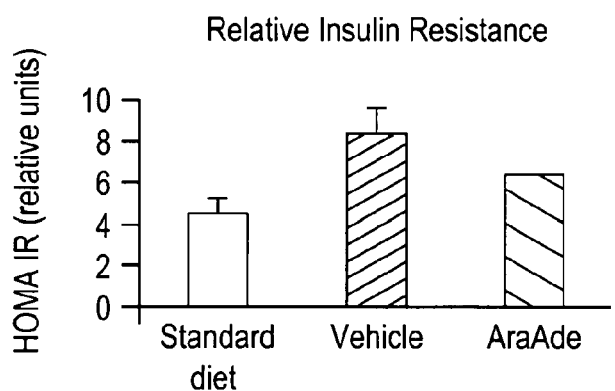
Figure 18C:
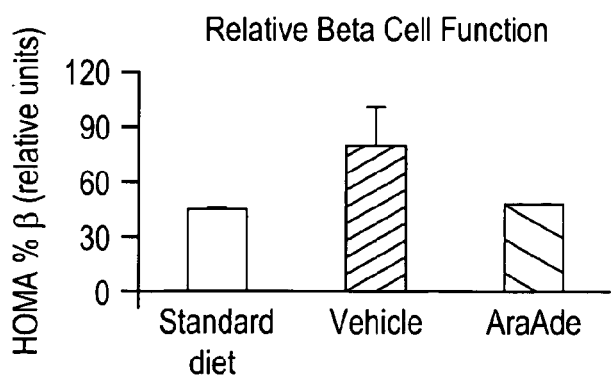

AraAde Improves Glucose Tolerance, Insulin Resistance and β-cell Function: In addition to the fasting blood glucose data shown above, the effect of AraAde on glucose tolerance in high-fat-diet fed mice was examined. All animals were placed on a high fat diet for 94 days and the treated animals received a total of 42 days of AraAde treatment or vehicle. AraAde-treated mice showed improved glucose tolerance (FIG. 18a). In order to evaluate insulin resistance, HOMA-IR, which is an index for insulin resistance, was calculated on terminal blood collected after a 6-7 hour fast. AraAde-treated mice showed a lower HOMA-IR than vehicle-treated mice and a similar HOMA-IR to standard diet-fed mice, suggesting improved insulin resistance by AraAde in these obese mice (FIG. 18b). HOMA β, an index of ability to secrete insulin in β-cell in the islets of Langerhans, was lower in AraAde-treated and standard diet-fed mice than in vehicle-treated mice, suggesting a compensatory increase of insulin secretion in response to increased insulin resistance and blood glucose levels in the vehicle treated group (FIG. 18c). Despite this increase in insulin secretion in the vehicle treated group, this group continues to exhibit higher fasting glucose levels (FIG. 17a) and a lower glucose tolerance.

Figure 19:
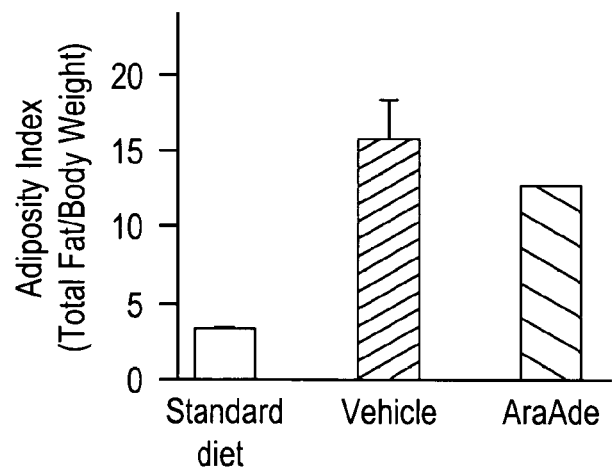
FIG. 19 demonstrates that mice on 94 days of a high fat diet when treated with AraAde for 42 days showed a clear lower percentage of body fat when compared against the vehicle treated group.

AraAde Decreases Accumulation of Fat in Adipose Tissue: The size of various fat pads was smaller in AC5 KO compared to WT mice. The effect of AraAde on fat accumulation in adipose tissue was examined. The AraAde-treated group showed a lower adiposity index (FIG. 19).

Inhibition of AC5 Increases Exercise Capacity: AC5 KO and WT mice were exercised on a treadmill. Exercise performance was measured using the maximal distance and the work to exhaustion. AC5 KO mice exhibit increased exercise capacity compared to WT mice, as measured by increased maximal distance and work to exhaustion, higher $VO_{2max}$ and lower respiratory exchange ratio ($RER_{max}$). In addition, in a chronically instrumented, conscious mice model, there is no significant difference in cardiac output between AC5 KO and WT mice during exercise, demonstrating that AC5 inhibition permits enhanced exercise performance independent of cardiac output. An in vitro study indicates that inhibition of AC5 increases exercise capacity through improved mitochondrial oxidative capacity and biogenesis. Inhibition of AC5 by AraAde increases exercise tolerance after chronic ISO infusion. However, in these mice, LVEF was also higher in the AraAde treatment group.

Drugs With Adenosine-Like Structures have an AC5 Inhibitory Effect

Figure 9:
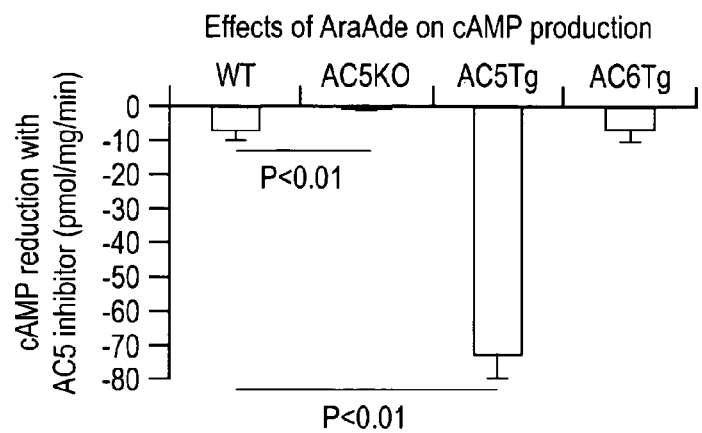
FIG. 9 demonstrates a method of screening for AC5 inhibitors. AraAde inhibits cAMP production in hearts from AC5 Tg but not AC6 Tg. Membrane preparations of the hearts were incubated with 32P-ATP in the presence of AraAde and forskolin (Fsk; 50 mM), a direct AC stimulator. Formed 32P-cAMP was then measured. n=4. *$p<0.01$ vs. WT.
Figure 10:
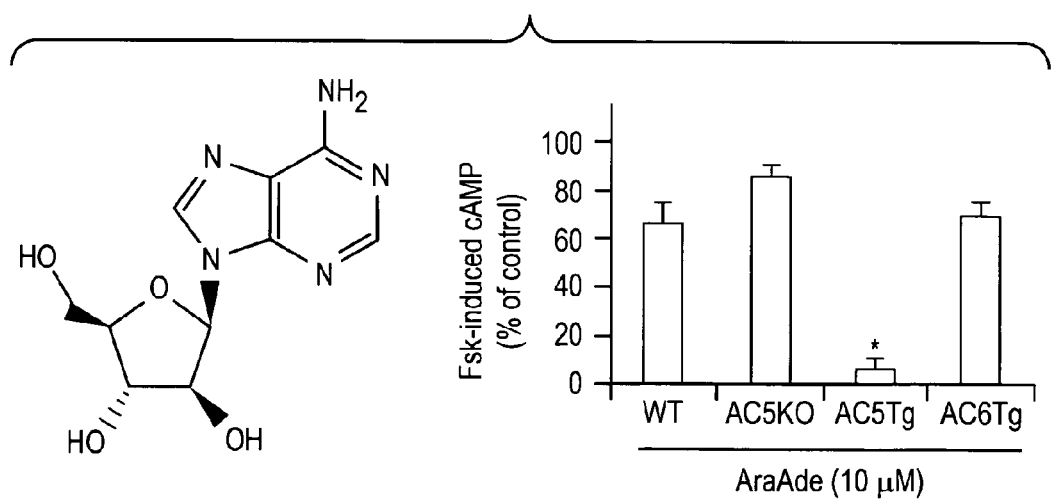
FIG. 10 demonstrates that AraAde inhibits cAMP production in hearts from AC5 Tg but not AC6 Tg.

Several commercially available drugs with an adenosine like structure, which is required for binding to and inhibiting AC, for potential AC5 inhibitors, were screened, and several commercial and experimental drugs that show AC5 inhibition were found. To measure AC5 inhibition, in addition to membrane preparations from mouse heart, membrane preparations from mouse striatum were used because AC5 provides about 80% of total AC activity in the striatum, mimicking purified AC5. cAMP was measured with 50 mM forskolin (FSK) in the presence or absence of 10 mM of the indicated drugs). Since the catalytic site of AC is in the intracellular domain, the plasma membrane permeability of these drugs was examined using H9C2 cells, a cardiac myoblast cell line (FIG. 9) cAMP accumulation is shown in H9C2 cells. Cells were stimulated with 5 mM ISO, a b-adrenergic receptor agonist, for 3 minutes in the presence or absence of 10 mM of the indicated drugs. AraAde is an anti-herpes simplex drug and 2'5'ddAdo is an experimental drug.). These inhibitors also show AC inhibition in H9C2 suggesting that these drugs exert the AC inhibitory effects when administered in vivo. Several drugs with the adenine-like structure for AC5 inhibitors were screened using recombinant proteins of several AC subtypes with a baculovirus overexpression system. Furthermore, forskolin induced cAMP production was dramatically decreased in the presence of the AC5 inhibitor, AraAde, but only in the hearts from mice with overexpressed AC5 (AC5 transgenic, Tg) and not AC6 Tg (another major cardiac AC isoform) (FIG. 10). AraAde inhibits cAMP production in the hearts from AC5 Tg but not AC6 Tg. Membrane preparations of the hearts were incubated with 32P-ATP in the presence of AraAde and forskolin (FSK; 50 mM), a direct AC stimulator. Formed 32P-cAMP was then measured. n=4. *p<0.01 vs. WT.). These studies demonstrate the inhibitor selectivity for AC5 compared to other subtypes.

AraAde is a Selective Inhibitor of the AC5 Isoform

We demonstrated above that, in the heart, AraAde selectively inhibits AC5 but not AC6. To further explore selectivity, we compared the $IC_{50}$ of AraAde for AC2, AC3 and AC5. These isoforms represent all 3 major AC subtypes. Table 1 shows that AraAde is highly selective for AC5.

AC5 Inhibitor Prevents ISOproterenol-induced Apoptosis without Impairing Contraction in Cultured Cardiac Myocytes Isoproterenol (ISO) induced accumulation of cAMP in the heart is suppressed by 30% in AC5 KO mice, indicating that AC5 accounts for 30% of ISO-induced cAMP production in the heart. cAMP accumulation in mouse cardiac myocytes, from AC5 KO and WT mice, was measured with increasing ISO concentrations. Decreases in cAMP in AC5 KO were observed only at high ISO concentrations. AC5 inhibitors, 2'5' dideoxyadenosine (2'5'ddAdo) and AraAde achieved dose-dependent suppression of ISO-induced cAMP accumulation in cardiac myocytes. The maximum level of suppression by 2'5'ddAdo and AraAde was around 30%, which is consistent with the notion that they inhibit AC5. Furthermore, these AC5 inhibitors were shown to prevent apoptosis without impairing contraction in cultured cardiac myocytes, suggesting that AC5 inhibition is protective. 2'5'ddAdo and AraAde also prevented ISO induced apoptosis in cultured cardiac myocytes. (Toya et al., *J Mol Cell Cardiol.*, 1998; 30(1):97-108)

AC5 Inhibitor Prevents LV Dysfunction and Apoptosis in the Chronic ISO Infusion Model The effect of AraAde and 2'5'ddAdo, on the cardiac phenotype induced by chronic ISO infusion was examined. ISO (60 mg/g/day) with or without the AC5 inhibitor AraAde (200 mg/g/day) was chronically infused with an osmotic mini-pump for 1 week in C57Bl/6 mice. Mice were then subjected to echocardiography (LVEF) (A); and tissue was harvested for pathological examination of myocardial apoptosis (by TUNEL) (B); and fibrosis (by PASR) (C). n=4-9.*p<0.05 vs. all other groups. AraAde (20 mg/kg/day for 1 week) inhibited the chronic ISO-induced decreases in left ventricular ejection fraction (LVEF). In addition, AraAde (100 µg/g/day) significantly inhibited ISO-induced myocardial apoptosis, and cardiac fibrosis. Thus, this AC5 inhibitor is protective against the development of ISO-induced cardiomyopathy.

Formulations and Methods of Administration

A pharmaceutical composition useful in the present invention comprises an AC5 inhibitor and a pharmaceutically acceptable carrier, excipient, diluent and/or salt. Pharmaceutically acceptable carrier, diluent, excipient and/or salt means that the carrier, diluent, excipient and/or salt must be compatible with the other ingredients of the formulation, does not adversely affect the therapeutic benefit of the AC5 inhibitor, and is not deleterious to the recipient thereof.

Administration of the compounds or pharmaceutical compositions thereof for practicing the present invention can be by any method that delivers the compounds systemically. These methods include oral routes, parenteral routes, intraduodenal routes, etc.

For topical applications, the compound or pharmaceutical composition thereof can be formulated in a suitable ointment containing the active component suspended or dissolved in one or more carriers. Carriers for topical administration of the compounds of this invention include, but are not limited to, mineral oil, liquid petrolatum, white petrolatum, propylene glycol, polyoxyethylene, polyoxypropylene compound, emulsifying wax, sugars such as lactose and water. Alternatively, the pharmaceutical compositions can be formulated in a suitable lotion or cream containing the active components suspended or dissolved in one or more pharmaceutically acceptable carriers. Suitable carriers include, but are not limited to, mineral oil, sorbitan monostearate, polysorbate 60, cetyl esters wax, cetearyl alcohol, 2-octyldodecanol, benzyl alcohol and water.

Depending on the particular condition, disorder or disease to be treated, additional therapeutic agents can be administered together with the AC5 inhibitor. Those additional agents can be administered sequentially in any order, as part of a multiple dosage regimen, from the AC5 inhibitor-containing composition (consecutive or intermittent administration). Alternatively, those agents can be part of a single dosage form, mixed together with the AC5 inhibitor in a single composition (simultaneous or concurrent administration).

For oral administration, a pharmaceutical composition useful in the invention can take the form of solutions, suspensions, tablets, pills, capsules, powders, granules, semisolids, sustained release formulations, elixirs, aerosols, and the like. Tablets containing various excipients such as sodium citrate, calcium carbonate and calcium phosphate are employed along with various disintegrants such as starch, preferably potato or tapioca starch, and certain complex silicates, together with binding agents such as polyvinylpyrrolidone, sucrose, gelatin and acacia. Additionally, lubricating agents such as magnesium stearate, sodium lauryl sulfate and talc are often very useful for tabletting purposes. Solid compositions of a similar type are also employed as fillers in soft and hard-filled gelatin capsules; preferred materials in this connection also include lactose or milk sugar as well as high molecular weight polyethylene glycols. When aqueous suspensions and/or elixirs are desired for oral administration, the compounds of this invention can be combined with various sweetening agents, flavoring agents, coloring agents, emulsifying agents and/or suspending agents, as well as such diluents as water, ethanol, propylene glycol, glycerin and various like combinations thereof. The choice of formulation depends on various factors such as the mode of drug administration (e.g., for oral administration, formulations in the form of tablets, pills or capsules are preferred) and the bioavailability of the drug substance.

A suitable pharmaceutical composition for parenteral injection can comprise pharmaceutically acceptable sterile aqueous or nonaqueous solutions, dispersions, suspensions or emulsions as well as sterile powders for reconstitution into sterile injectable solutions or dispersions just prior to use. Aqueous solutions are especially suitable for intravenous, intramuscular, subcutaneous and intraperitoneal injection purposes. In this connection, the sterile aqueous media employed are all readily obtainable by standard techniques well-known to those skilled in the art. Examples of suitable aqueous and nonaqueous carriers, diluents, solvents or vehicles include water, ethanol, polyols (such as glycerol, propylene glycol, polyethylene glycol, and the like), carboxymethylcellulose and suitable mixtures thereof, vegetable oils (such as olive oil), and injectable organic esters such as ethyl oleate. Proper fluidity can be maintained, for example, by the use of coating materials such as lecithin, by the maintenance of the required particle size in the case of dispersions, and by the use of surfactants.

The pharmaceutical compositions useful in the present invention can also contain adjuvants such as, but not limited to, preservatives, wetting agents, emulsifying agents, and dispersing agents. Prevention of the action of microorganisms can be ensured by the inclusion of various antibacterial and antifungal agents, such as for example, paraben, chlorobutanol, phenol sorbic acid, and the like. It can also be desirable to include isotonic agents such as sugars, sodium chloride, and the like. Prolonged absorption of the injectable pharmaceutical form can be brought about by the inclusion of agents that delay absorption such as aluminum monostearate and gelatin.

Injectable depot forms are made by forming microencapsule matrices of the drug in biodegradable polymers such as polylactide, polyglycolide, and polylactide-polyglycolide. Depending upon the ratio of drug to polymer and the nature of the particular polymer employed, the rate of drug release can be controlled. Examples of other biodegradable polymers include poly(orthoesters) and poly(anhydrides). Depot injectable formulations are also prepared by entrapping the drug in liposomes or microemulsions that are compatible with body tissues.

The injectable formulations can be sterilized, for example, by filtration through a bacterial-retaining filter, or by incorporating sterilizing agents in the form of sterile solid compositions which can be dissolved or dispersed in sterile water or other sterile injectable medium just prior to use.

Suspensions, in addition to the active compounds, can contain suspending agents as, for example, ethoxylated isostearyl alcohols, polyoxyethylene sorbitol and sorbitan esters, microcrystalline cellulose, aluminum metahydroxide, bentonite, agar-agar, and tragacanth, and mixtures thereof.

For purposes of transdermal (e.g., topical) administration, dilute sterile, aqueous or partially aqueous solutions (usually in about 0.1% to 5% concentration), otherwise similar to the above parenteral solutions, are prepared.

The pharmaceutical compositions useful in the invention can also be administered by nasal aerosol or inhalation. Such compositions are prepared according to techniques well-known in the art of pharmaceutical formulation and can be prepared as solutions in saline, employing benzyl alcohol or other suitable preservatives, absorption promoters to enhance bioavailability, fluorocarbons, and/or other conventional solubilizing or dispersing agents.

In nonpressurized powder compositions, the active ingredients in finely divided form can be used in admixture with a larger-sized pharmaceutically acceptable inert carrier comprising particles having a size, for example, of up to 100 μm in diameter. Suitable inert carriers include sugars such as lactose. Desirably, at least 95% by weight of the particles of the active ingredient have an effective particle size in the range of 0.01 to 10 μm.

Alternatively, the composition can be pressurized and contain a compressed gas, such as, e.g., nitrogen, carbon dioxide or a liquefied gas propellant. The liquefied propellant medium and indeed the total composition are preferably such that the active ingredients do not dissolve therein to any substantial extent. The pressurized composition can also contain a surface active agent. The surface active agent can be a liquid or solid non-ionic surface active agent or can be a solid anionic surface active agent. It is preferred to use the solid anionic surface active agent in the form of a sodium salt.

Compositions for rectal or vaginal administration are preferably suppositories which can be prepared by mixing the compounds of the invention with suitable non-irritating excipients or carriers such as cocoa butter, polyethylene glycol or a suppository wax which are solid at room temperature but liquid at body temperature and therefore melt in the rectum or vaginal cavity and release the drugs.

The compositions useful in the present invention can also be administered in the form of liposomes. As is known in the art, liposomes are generally derived from phospholipids or other lipid substances. Liposomes are formed by mono- or multi-lamellar hydrated liquid crystals that are dispersed in an aqueous medium. Any non-toxic, physiologically acceptable and metabolizable lipid capable of forming liposomes can be used. The present compositions in liposome form can contain, in addition to the compounds of the invention, stabilizers, preservatives, excipients, and the like. The preferred lipids are the phospholipids and the phosphatidyl cholines (lecithins), both natural and synthetic. Methods to form liposomes are known in the art (e.g., Prescott, *Meth. Cell Biol.* 14:33 (1976)).

Other pharmaceutically acceptable carrier includes, but is not limited to, a non-toxic solid, semisolid or liquid filler, diluent, encapsulating material or formulation auxiliary of any type, including but not limited to ion exchangers, alumina, aluminum stearate, lecithin, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat.

Solid pharmaceutical excipients include, but are not limited to, starch, cellulose, talc, glucose, lactose, sucrose, gelatin, malt, rice, flour, chalk, silica gel, magnesium stearate, sodium stearate, glycerol monostearate, sodium chloride, dried skim milk and the like. Liquid and semisolid excipients can be selected from glycerol, propylene glycol, water, ethanol and various oils, including those of petroleum, animal, vegetable or synthetic origin, e.g., peanut oil, soybean oil, mineral oil, sesame oil, etc. Preferred liquid carriers, particularly for injectable solutions, include water, saline, aqueous dextrose, and glycols.

Methods of preparing various pharmaceutical compositions with a certain amount of active ingredient are known, or will be apparent in light of this disclosure, to those skilled in this art. Other suitable pharmaceutical excipients and their formulations are described in Remington's Pharmaceutical Sciences, edited by E. W. Martin, Mack Publishing Company, 19th ed. (1995).

Pharmaceutical compositions useful in the present invention can contain 0.1%-95% of the compound(s) of this invention, preferably 1%-70%. In any event, the composition or formulation to be administered will contain a quantity of a compound(s) according to this invention in an amount effective to treat the condition, disorder or disease of the subject being treated.

One of ordinary skill in the art will appreciate that pharmaceutically effective amounts of the AC5 inhibitor can be determined empirically and can be employed in pure form or, where such forms exist, in pharmaceutically acceptable salt, ester or prodrug form. The agents can be administered to a patient as pharmaceutical compositions in combination with one or more pharmaceutically acceptable excipients. It will be understood that, when administered to, for example, a human patient, the total daily usage of the agents or composition of the present invention will be decided within the scope of sound medical judgment by the attending physician. The specific therapeutically effective dose level for any particular patient will depend upon a variety of factors: the type and degree of the cellular response to be achieved; activity of the specific agent or composition employed; the specific agents or composition employed; the age, body weight, general health, sex and diet of the patient; the time of administration, route of administration, and rate of excretion of the agent; the duration of the treatment; drugs used in combination or coincidental with the specific agent; and like factors well known in the medical arts. For example, it is well within the skill of the art to start doses of the agents at levels lower than those required to achieve the desired therapeutic effect and to gradually increase the dosages until the desired effect is achieved.

For example, satisfactory results may be obtained by oral administration of the compounds at dosages on the order of from 0.05 to 500 mg/kg/day, preferably 0.1 to 100 mg/kg/day, more preferably 1 to 50 mg/kg/day, administered once or, in divided doses, 2 to 4 times per day. On administration parenterally, for example, by i.v. bolus, drip or infusion, dosages on the order of from 0.01 to 1000 mg/kg/day, preferably 0.05 to 500 mg/kg/day, and more preferably 0.1 to 100 mg/kg/day, can be used. Suitable daily dosages for patients are thus on the order of from 2.5 to 500 mg p.o., preferably 5 to 250 mg p.o., more preferably 5 to 100 mg p.o., or on the order of from 0.5 to 250 mg i.v., preferably 2.5 to 125 mg i.v. and more preferably 2.5 to 50 mg i.v.

Dosaging can also be arranged in a patient specific manner to provide a predetermined concentration of the agents in the blood, as determined by techniques accepted and routine in the art (HPLC is preferred). Thus patient dosaging can be adjusted to achieve regular on-going blood levels, as measured by HPLC, on the order of from 50 to 5000 ng/ml, preferably 100 to 2500 ng/ml.

In the adult, the doses are generally from about 0.001 to about 100, preferably about 0.001 to about 50, mg/kg body weight per day by inhalation, from about 0.01 to about 100, preferably 0.1 to 70, more especially 0.5 to 20, 30, 40, 50 or 60, mg/kg body weight per day by oral administration, and from about 0.001 to about 70, preferably 0.01 to 10, 20, 30, 40 or 50, mg/kg body weight per day by intravenous administration. In each particular case, the doses are determined in accordance with the factors distinctive to the patient to be treated, such as age, weight, general state of health and other characteristics, which can influence the efficacy of the compound according to the invention.

DETAILED DESCRIPTION OF THE PREFERRED EMBODIMENTS

EXAMPLE 1

Generation of Knockout Mice

The targeting construct was prepared by ligating a 2.2-kb XhoI-PstI fragment from the 5' end of the type 5 AC gene, containing the exon with the first translation initiation site (5'-arm), a 1.7-kb fragment containing a neomycin resistance gene fragment (neo) driven by a phosphoglycerate kinase (PGK) promoter, and a BssHII-NcoI 7.0-kb fragment of the type 5 AC gene (3'-arm), into pBluscript II KS (Stratagene, La Jolla, Calif., USA). The type 5 AC gene has another translational start site accompanied by a reasonable Kozak consensus sequence located 738-bp downstream of the first translational start site within the same exon. To impair the second site, inventors excised a 0.15 kb PstI-BssHII fragment containing the second ATG and replaced it with a PGK-neo cassette in the final targeting vector as described in U.S. Ser. No. 10/429,214, the disclosure of which is incorporated herein by reference.

Embryonic stem cells were transfected with 50 μg linearized targeting vector by electroporation (Bio-Rad Gene pulsar set at 250 V and 960° F.). G418 (200 μg/ml) selection was applied 48 hours after transfection and resistant clones were isolated after 7-10 days of transfection. Subsequently, inventors obtained 576 clones. Genomic DNA from these resistant clones was digested with KpnI and probed with a 5' probe. Digesting genomic DNA with BamHI and probing with a 3' probe reconfirmed 8 positive clones. A single integration of the targeting vector was confirmed by a neo-probe. Two clones (clones #314 and #378) were injected into C57BL/6 blastocysts and chimeras were obtained. These chimeras successfully allowed germ-line transmission and were crossed with C57BL/6 females. F1-heterozygous offspring were then interbred to produce homozygous mutations. All mice were 129/SvJ-C57BL/6 mixed background litter mates from F1 heterozygote crosses. All experiments were performed in 4-6 month old homozygous AC5KO and wild-type (WT) littermates.

Rotor Rod Test

The locomotor activity of intact animals, AC5KO versus WT was examined. At first glance the animals appeared normal, being neither catatonic nor rigid. However, standard behavior tests revealed that the mice had a significant impairment in motor function. The mice were studied using a rotor rod test in which mice were placed on a rotating rod and had to make continuous adjustment in balance in order to remain upright. The time that the mice spent on the accelerating rotor rod without falling was measured. The rod increased from 3 rpm to 30 rpm during each 5 min. trial. Each mouse went through 5 trials, which showed a gradual increase in the time on a rod showing "learning effects". There was no significant difference between WT and Hetero at the $1^{st}$ through $4^{th}$ trial. At the $5^{th}$ trial, there was a small but significant decrease in their performance in Hetero. AC5KO, by contrast, showed a significant improvement at the $1^{st}$ trial and constantly had and constantly has a shorter time on a rotor rod with poor learning effect, suggesting that the locomotor activity in AC5KO was significantly impaired.

RNase Protection Assay

Partial fragments of mouse AC cDNA clones for each isoform (types 1-9) were obtained by PCR. Sequencing and restriction mapping verified these cDNA fragments. Total RNA was isolated using RNeasy Midi kit (QIAGEN, Valencia, Calif., USA). Single strand cDNA was synthesized from total RNA using reverse transcriptase. The plasmid constructs were linearized by appropriate restriction enzyme. $^{32}$P-labeled cRNA probes were then generated using the Riboprobe Systems (Promega, Madison, Wis., USA). A human 28S ribosomal RNA probe was used as an internal control. RNase protection assay was performed using the RPA III kit (Ambion, Austin, Tex., USA) as suggested by the manufacture, followed by analysis on a 5% polyacrylamide-urea gel. Gels were exposed to X-OMAT film (Kodak, Rochester, N.Y., USA) for quantitation.

AC Assay and Tissue cAMP Measurement

Hearts were dissected from the mice and membrane preparations were prepared as described previously. Protein concentration was measured by the method of Bradford using bovine serum albumin as a standard. AC activity was measured as described previously. AC activity was linear within the incubation time up to 30 min. In order to harvest hearts for tissue cAMP content measurements, mice were allowed to acclimate to the surroundings in the laboratory for an hour before sacrifice. Freshly isolated hearts were briefly immersed in liquid nitrogen. The tissue was homogenized in ice-cold 6% percholic acid, and cAMP was extracted as described before. The concentration of cAMP was determined with an RIA kit (PerkinElmer Life Sciences, Boston, Mass., USA).

Physiological Studies

AC5KO (6.4+/−0.2 month old, n=6) and WT (6.7+/−0.1 month old, n=6) of either sex from the same genetic background as the transgenic mice were used for the physiological studies. Measurements of LV ejection fraction (LVEF) were performed as described previously. Briefly, after determination of body weight, mice were anesthetized with ketamine (0.065 mg/g), acepromazine (0.002 mg/g), and xylazine (0.013 mg/g) injected intraperitoneally and were allowed to breathe spontaneously. Echocardiography was performed using ultrasonography (Sequoia C256; Acuson Corporation, Mountain View, Calif., USA). A dynamically focused 15-MHz annular array transducer was applied from below, using a warmed saline bag as a standoff. M-mode echocardiographic measurements of the LV were performed at baseline and during intravenous infusion of ISO (0.005, 0.01, 0.02, and 0.04 µg/kg/min i.v. for 5 minutes each) (Abbott Laboratories Inc, North Chicago, Ill., USA) using an infusion pump (PHD 2000; Harvard Apparatus, Inc., Holliston, Mass., USA). The total amount of the infusion volume was <100 µL in each mouse. On a separate occasion, each mouse received an infusion of saline as a control to ensure that the volume of infusion alone did not contribute to enhance ventricular performance. To examine the responses to a muscarinic agonist, intraperitoneal (i.p.) infusion of Ach (25 mg/kg) was performed on top of the i.v. infusion of ISO (0.04 µg/kg/min).

In AC5KO and WT mice, four ECG wires (New England Electric Wire Corporation, Lisbon, N.H., USA) were placed subcutaneously, a silicone elastomer tubing (Cardiovascular Instrument Corp., Wakefield, Mass., USA) was inserted into the right external jugular vein and a 1.4 F micromanometer catheter (Millar Instruments, Inc., Houston, Tex., USA) was inserted into the lower abdominal aorta via the femoral artery as described previously with some modifications. The ECG wires, the silicone elastomer tubing and the micromanometer catheter were tunneled subcutaneously to the back, externalized, and secured in a plastic cap. On the day of the study, each mouse was placed in the mouse holder, the jugular venous catheter was accessed and connected to a microliter syringe (Hamilton Co., Reno, Nev., USA), the 1.4 F micromanometer catheter was connected to a recorder (Dash 4u; Astro-Med, Inc., West Warwick, R.I., USA) and the ECG wires were connected to an ECG amplifier (Gould Inc., Cleveland, Ohio, USA). All experiments were recorded with animals in the conscious state. After at least 6 hours recovery from the implantation of the catheter, when a stable heart rate (HR) was achieved, the baseline ECG and arterial pressure (AP) were recorded for 5 min. Ach (0.05 µg/g) was then administered intravenously (i.v.), and the ECG and AP recording were repeated. A recovery period of 15 min was allowed for the HR and AP to return to baseline before administering the next drug. Baseline HR slowing was examined in response to phenylephrine (0.2 µg/g i.v.).

Statistics

All data are reported as mean+/−SEM. Comparisons between AC5KO and WT values were made using a t-test. $P<0.05$ was taken as a minimal level of significance.

Results:

Targeted Disruption of the Type 5 AC Gene.

The type 5 AC gene was disrupted in mice using homologous recombination as described in U.S. Ser. No. 10/429,214, the disclosure of which is incorporated herein by reference. Mice were genotyped by Southern blotting using genomic DNA from tail biopsies. mRNA expression of the type 5 AC in heterozygous mice was approximately half of that in WT and it was undetectable in AC5KO. The growth, general appearance and behavior were similar to those of WT.

No Compensatory Increase in the Other Isoforms of AC.

Whether there were compensatory increases in the expression of the other isoforms of AC in AC5KO was investigated. Since AC isoform antibodies that can convincingly determine the level of protein expression of all the isoforms are not available, inventors quantitated the mRNA expression of the AC isoforms by an RNase protection assay. cRNA of the 28S ribosomal RNA was used as an internal control. Types 3, 4, 6, 7 and 9 AC were readily detected, but not increased, while types 1, 2, and 8 were hardly detectable, arguing that type 6 AC, a homologue of type 5 AC in the heart, could not compensate for the type 5 AC deficiency. AC activity was decreased in the hearts of AC5KO in vitro.

cAMP production in membranes from the hearts of AC5KO and WT at 6 months of age was examined. The steady state AC activity was determined as the maximal capacity of cAMP production in the presence of ISO (100 µM ISO+100 µM GTP), GTPγS (100 µM) or forskolin (100 µM). AC activity was decreased in AC5KO relative to that in WT by 35+/−4.3% (basal), 27+/−4.6% (ISO), 27+/−2.4% (GTPγS), and 40+/−4.7% (forskolin). These data indicate that type 5 AC, as the major isoform in the heart, is responsible for approximately 30-40% of total AC activity in the mouse heart. However, cardiac tissue cAMP content was not significantly decreased in AC5KO compared to WT (55+/−7.5 vs 62+/−3.4 pmol/mg protein, respectively, n=4, p=NS). Carbachol (10 µM), a muscarinic agonist, decreased ISO-stimulated AC activity by 21+/−3.4% in WT, but did not inhibit ISO-stimulated AC activity in AC5KO. Basal cardiac function was not decreased, but the response to ISO and muscarinic inhibition of ISO were attenuated.

The cardiac responses to i.v. ISO on LVEF and fractional shortening (FS) in AC5KO were attenuated as expected (data not shown, Okumura et al. Circulation.116(16):1776-1783). However, baseline cardiac function tended to be increased; LVEF (WT vs. AC5KO; 59+/−2.4% vs. 64+/−4.3%) and FS (26+/−1.4% vs. 29+/−2.7%). Muscarinic inhibition of ISO stimulated cardiac function, as measured by LVEF, was prominent in WT, as expected, but was abolished in AC5KO.

EXAMPLE 2

Adenine or its Analogs Inhibit AC5

As described previously in U.S. Ser. No. 10/429,214, the disclosure of which is incorporated herein by reference, "HI30435" showed a high selectivity to inhibit AC5. The result from a dose-response analysis and the determination of the IC50 values are discussed below.

Selectivity among the AC isoforms was determined. The relative potency of HI30435, in comparison to classic AC inhibitor (3'-AMP) is shown as an example. HI30435 potently inhibited AC5 while that inhibited AC2 and AC3 only to a modest degree. The $IC_{50}$ values were calculated to be 0.32 µM for AC5, 11.1 µM for AC3, 65.3 µM for AC2. The selectivity ratio of HI30435 was 207 between AC5 and AC2. 3'-AMP showed a weak selectivity for AC5 in inhibiting AC catalytic activity. The $IC_{50}$ values were calculated to be 14.6 µM for AC5, 30.2 µM for AC3, 263 µM for AC2. The selectivity ratio was 18 between AC5 and AC2. These data suggest that HI30435 is extremely specific and strong inhibitor for AC5. Most importantly, HI30435, but not NKY80, inhibited cAMP accumulation in intact H9C2 cells. This suggests that membrane penetration of these compounds is important for biological activity and that HI30435, but not NKY80, has such a capability.

EXAMPLE 3

Research Design and Methods

Mice: Experiments will be performed in 8 week-old male C57BL/6 mice (n=8/group). There will be a 7-day acclimation period with access to standard normal chow and water ad libitum after mice arrive at the institution.

Subcutaneous Implantation of Osmotic Pump: Mice will be treated for 3.5 or 5 months with vehicle (DMSO) or AraAde dissolved in DMSO (20 mg/kg/day) via a subcutaneously implanted Alzet mini-osmotic pump (Model 2004, which allows for a 30 day infusion, ALZET Osmotic Pumps, Cupertino, Calif.). Pumps will be replaced every 30 days. Mice will be anesthetized with a mixture of Ketamine/ Acepromazine/Xylazine mixture (dose (mg/kg): 65 mg/kg/2 mg/kg /13 mg/kg, respectively, IP) or with filtered Avertin 2.5% (0.29 mg/kg, IP). A 2 cm transverse incision will be made lateral to the midscapular line on the side of the mouse and the subcutaneous space will be created by undermining the skin with a pair of blunt-tip scissors in the left lower back large enough to accommodate the implant. The osmotic pump will be inserted into the pouch with the flow moderator facing away from the skin incision. The skin incision will be either closed with 5-0 nylon sutures with the knots buried beneath the skin or with stainless steel wound clips. The midscapular position will not be used to avoid disturbing the interscapular brown fat pad, which is a critical measurement. A transcutaneous suture will be then placed in mid-back to help avoid the possibility of the subcutaneous pump migrating to the other side. The animal will be allowed to recover in a warm Thermocare unit.

Diets: Based on publicly available data a high fat diet (35.5% fat, 5.447 kcal/gram) that is capable of inducing at least a 15% weight gain over a 1 month period, consistent with the literature (Messier, et al., *Behav Brain Res,* 2007, 178(1): 139-145; Challis, et al., *Proc Natl Acad Sci USA,* 2004, 101(13): 4695-4700) will be used. Furthermore, previous work on diet induced obesity and diabetes have shown that C57BL/6J mice when placed on high fat diet will develop approximately 45% increase in body weight, 40% increase in fasting blood glucose levels and a 316% increase in plasma insulin levels versus control, by the 15$^{th}$ week of the high fat diet, indicating the development of diabetes (Bender, et al., *Diabetes Obes Metab,* 2007, 9(5): 688-696). Experiments will then be performed using (1) a standard control diet and (2) a high fat diet (HFD). The diets come prepared at the above specified fat concentrations and will be purchased from Bio-Serv. (Frenchtown, N.J.). Up to four animals will be housed together. After feeding, animals will be monitored for 5-10 min to ensure they begin eating. Cages will be checked for pieces of food and these pieces will then be transferred to new cages when bedding changes occur. High fat diets have previously been shown to induce both obesity and diabetes (Petro, et al., *Metabolism,* 2004, 53(4): 454-457).

Body Weight and Food Measurements: Total body weight and food intake will be measured weekly for 3.5 months. Body weight will be measured weekly starting at day 0. Body weight change and food intake as a function of time will be statistically analyzed to detect significant weight differences between groups. Diet intake will be obtained by subtracting the weight of the remaining diet from the initially supplied diet.

Blood Glucose, Growth Hormone, Insulin, Free Fatty Acids (FFA) and Serum Leptin: On a weekly basis, mice will be fasted for a 6 hour period and blood will be drawn from venous tail puncture. From these samples, blood glucose will be measured by an enzymatic method (Autokit Glucose, Wako Chemicals USA), insulin levels will be measured by ELISA (Crystal Chem, Dovers Grove, Ill.), growth hormone, leptin levels in serum of mice will be measured using a commercially available ELISA and a recombinant mouse leptin standard (R&D Systems, Inc.), and FFA's will be measured using the HR Series NEFA-HR (Wako Chemicals USA).

Glucose Tolerance and Insulin Resistance: On a monthly basis, mice will be fasted for a period of 12 hours before analyzing the insulin sensitivity and glucose tolerance (Nomiyima, et al., *J Clin Invest,* 2007, 117(10): 2877-2888). A 200-µl blood sample via tail vein will be drawn for insulin (ELISA) and glucose measurement immediately with a glucometer (Dex, Bayer). A dose of dextrose (50% solution, 1 g/kg body wt) will be injected intraperitoneally, and blood will be drawn at 15, 30, 45, and 60 min for insulin and glucose determination. Insulin resistance index will be calculated as the product of the areas under the glucose and insulin curves (AUCglucose×AUCinsulin) as previously described (Sambandam, et al., *Heart Fail Rev,* 2002, 7(2):161-173).

Exercise: Mice will be treadmill-tested, on a monthly basis, to measure indices defining exercise capacity. All mice will be given 1 practice trial 3 days before the experiment to adapt to the treadmill-testing environment but otherwise will be kept sedentary. At the time of treadmill testing, each mouse will be placed on a treadmill at a constant 10° angle enclosed by a metabolic chamber through which air flow passes at a constant speed (Oxymax 2, Columbus Instruments). $O_2$ and $CO_2$ gas fractions will be monitored at both the inlet and output ports of the metabolic chamber. After a 30-min period of acclimatization, basal measurements will be obtained over a period of 5 min. The treadmill will then be started at 4 m/min, and the speed will be incrementally increased 2 m/min every 2 min until the mouse reached exhaustion. The treadmill protocol used in this study, which was chosen on the basis of previous data (Maxwell, et al., *Circulation,* 1998, 98(4):369-374), was designed so that the mice would quickly attain a plateau, reaching their maximal $VO_2$ before exhaustion. Exhaustion will be defined as spending time (10 sec) on the plate without attempting to reengage the treadmill.

VO$_2$, carbon dioxide production (VCO$_2$), and the respiratory exchange ratio (RER) will be calculated automatically every 30 sec by the Oxymax system. VO$_2$ and VCO$_2$ will be calculated by taking the difference between the input and output gas flow. RER will be calculated as VCO$_2$/VO$_2$. The maximal value from each mouse will be corrected by the work performed. Work is the product of the vertical running distance to exhaustion and body weight. A subgroup of these mice will be instrumented for measurement of CO and AP, so that stroke volume, CO, and TPR can be assessed.

Adipocyte Size: Adipocyte cell size will be compared in mice and quantified using the ImageProPlus (Media Cybernetics). Suitable cross sections will be defined as having circular capillary profiles and circular to oval adopocyte sections Calculation of Adiposity Index: Perigonadal, retroperitoneal, mesenteric and inguinal (on the side opposite of the subcutaneous osmotic pump) fat pads will be isolated and weighed (the single inguinal fat pad from the opposite side of the osmotic pump will be doubled) to calculate the adiposity index (total adipose depot weight/live body weight ×100).

Data Analysis and Statistics: All experiments will be performed using n=8 mice per group. Statistical comparisons among groups will be calculated using ANOVA with Bonferroni post hoc test. Comparisons between control and AraAde will be calculated using Student's t-test. P values of <0.05 will be considered significant.

EXAMPLE 4

Pharmacological Inhibition of AC5 will Reduce High Fat-induced Obesity in Mice.

Rationale: AraAde is an analog of adenosine with the D-ribose sugar replaced with D-arabinose and is a stereoisomer of adenosine. In addition, the concentration of AraAde used (20 mg/kg/day) is similar to, but slightly higher than that used clinically to treat systemic Herpes Simplex infection (15 mg/kg/day) in the past (*Physicians' Desk Reference* 1986: Medical Economics Company, 1986). AraAde is a selective inhibitor of AC5. AraAde attenuated cardiomyocyte apoptosis, and the progression of HF by chronic isoproterenol infusion. Furthermore, AraAde increased survival rate after myocardial infarction. AraAde is well tolerated when infused subcutaneously using a mini-osmotic pump for up to 3 months. Together with previous data showing AC5 KO mice ate more and weighed less (FIG. 3 and FIG. 4), and the ability of high fat diet to induce obesity (FIG. 13) and hyperglycemia (FIG. 14), inhibition of AC5 will ameliorate or lessen high fat induced obesity in mice.

Protocols: 8 week-old male C57BL/6 mice will be assigned to one of the two diet groups and undergo treatment with vehicle or AraAde for 3.5 months. Obesity will be defined as a body weight that is two standard deviations above the mean body weight of mice in the control diet group. For this aim, body weight and food intake will be measured weekly. A minimum of 15% weight difference between mice treated with chronic AC5 inhibitor versus their untreated and vehicle treated WT littermates will be documented. Additionally, perigodonadal, retroperitoneal, mesenteric and inguinal (on the side opposite of the subcutaneous osmotic pump) fat pads will be isolated and weighed (the inguinal fat pad weight will be doubled) to calculate adiposity index (total adipose depot weight/live body weight ×100) (Chiu, et al., *Physiol Genomics*, 2007, 31(1): 75-85) to help determine if the weight differences are due to difference in adipose tissue or lean muscle mass. Additionally, the weight ratio between the interscapular brown adipose fat pad and live body weight will be determined to monitor change in quantity of brown adipose tissue (Dong, et al., *Proc Natl Acad Sci USA*, 1997, 94(14): 7526-7530). These results will be further confirmed with histologic examination of the fat pads and determination of adipocyte size. The assumption will be the larger the adipocyte size, greater the adipose tissue growth.

Expected results: AraAde, a selective AC5 inhibitor, will ameliorate the high fat-induced obesity compared to vehicle. High-fat induced obesity in mice is preceded by hyperglycemia and hyperinsulinemia. Inhibition of AC5 by AraAde will ameliorate the development of insulin resistance in diabetes. The mice receiving the AC5 inhibitor will show an increase in exercise capacity as compared to the vehicle treated C57BL/6 mice. The mice fed a high fat diet will show a decrease in exercise capability as compared to WT. Treatment of mice on the HFD with AraAde will result in an increase in exercise capacity compared to mice on the HFD alone.

EXAMPLE 5

Protocols: Mice will be fed high-fat diet for 3 months to induce impaired glucose metabolism. Mice will be then subjected to AraAde treatment for 1 month. During the last week of the AraAde treatment, ISO will be chronically delivered. AraAde and ISO will be delivered with an implanted mini osmotic pump. Body weight, food intake, and fasting blood glucose will be monitored on a weekly basis. A glucose tolerance test will be performed on a monthly basis. Echocardiography will be performed before and after AraAde and ISO treatment. Insulin and triglycerides will be tested with terminal blood collection.

Number of animals: There will be 4 groups of mice, vehicle+vehicle, AraAde+vehicle, vehicle+ISO, AraAde+ISO. In each group, 16 mice will be used to calculate statistical significance. All the mice will be fed a high-fat diet. Therefore, 64 mice will be used.

Mice: Experiments will be performed in 8 week-old male C57BL/6 mice (n=16/group). There will be a 7-day acclimation period with access to standard normal chow and water ad libitum after mice arrive at the institution.

Diets: A high fat diet (35.5% fat, 5.447 kcal/gram) from Bio-Serv. (Frenchtown, N.J.) that is capable of inducing at least a 15% weight gain over a 1 month period, consistent with the literature (Messier, et al., *Behav Brain Res*, 2007, 178(1): 139-145), will be used.

Subcutaneous Implantation of Osmotic Pump: Drugs will be delivered via Alzet mini-osmotic pumps (Model 2004 for 4 weeks for AraAde (15 mg/kg/day), and Model 2001 for 1 week for ISO (60 mg/kg/day) (Okumura, et al., *Circulation*, 2007, 116(16): 1776-1783).

Body Weight and Food Measurements: Total body weight and food intake will be measured weekly.

Blood Glucose, Insulin and Triglycerides: On a weekly basis, mice will be fasted for a 6 hour period and blood will be drawn from venous tail puncture. Blood glucose will be measured by an enzymatic method (Autokit Glucose, Wako Chemicals USA). In terminal blood collection, insulin levels will be measured by ELISA (Crystal Chem, Dovers Grove, Ill.) and triglycerides will be measured using the ELISA kit (Wako Chemicals USA, Richmond, Va.).

Glucose Tolerance Test: On a monthly basis, mice will be fasted for a period of 6 hours before analyzing the glucose tolerance (Nomiyama, et al., *J Clin Invest*, 2007, 117(10): 2877-2888). A blood sample via tail vein will be drawn glucose measurement immediately with a glucometer (Dex, Bayer). A dose of dextrose (50% solution, 1 g/kg body wt)

will be injected intraperitoneally, and blood will be drawn at 0, 15, 30, 60, and 120 min for insulin and glucose determination.

Echocardiographic Measurement: Echocardiography measurement in mice is routine (Depre, et al., *Circ Res,* 2006, 98(2): 280-288); Yamamoto, et al., *J Clin Invest,* 2003, 111 (10): 1463-1474). LVEF will be calculated by the cubed methods (Depre, et al., *Circ Res,* 2006, 98(2): 280-288); Yamamoto, et al., *J Clin Invest,* 2003, 111(10): 1463-1474).

Histological Studies: Histological analyses for fibrosis and apoptosis will be performed as described by Okumura, et al., *PNAS,* 2003, 100(17) 9986-9990); Iwatsubo, et al., *J Biol Chem.,* 2004, 279(39): 40938-40945); (Depre, et al., *Circ Res,* 2006, 98(2): 280-288); Yamamoto, et al., *J Clin Invest,* 2003, 111(10): 1463-1474).

Survival Rate Analysis: Survival curves will be compared using Chi Square, Kaplan-Meier survival analysis or ANOVA with Fisher's PLSD test (Yan, et al., *Cell,* 2007, 130(2): 247-258). Regression lines will be compared for differences in slope using the Analysis of Covariance (ANCOVA). Significance will be accepted at $p<0.05$.

Data Analysis and Statistics: Statistical comparisons among groups will be calculated using one-way or two-way repeated ANOVA with Bonferroni post-hoc test. The P values of $<0.05$ will be considered significant.

Expected Results: AraAde will ameliorate the development of remodeling after chronic catecholamine stress as well as obesity and impaired glucose metabolism. In an ISO-treated group, AraAde will show: 1) higher survival rate, 2) higher LVEF, 3) lower myocardial apoptosis and 4) reduced cardiac fibrosis. In both an ISO-treated and -non-treated group, AraAde will show: 5) lower fasting blood glucose, 6) lower plasma insulin level, 7) lower plasma triglyceride levels, 8) improved glucose tolerance and 9) lower ratio of body weight to food intake, compared to vehicle.

EXAMPLE 6

Figure 20:
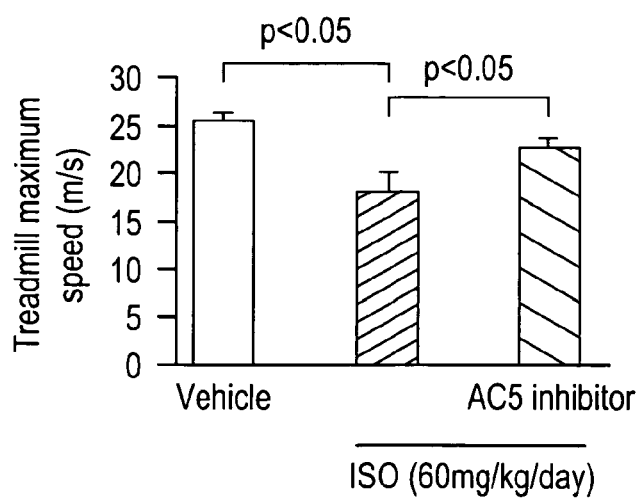
FIG. 20 demonstrates that AraAde increases exercise tolerance. The treadmill challenge by increasing running speed demonstrated that chronic ISO (60 mg/kg/day for 1 week) reduced the maximum speed at which the mice could run and that the AraAde (15 mg/kg/day) rescued exercise performance. n=4-6.
Figure 22:
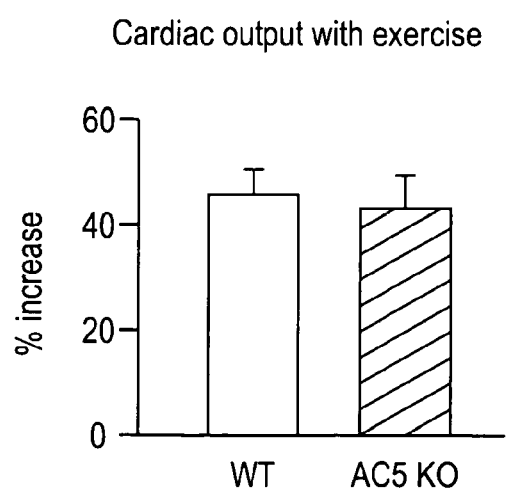
FIG. 22 demonstrates cardiac output in AC5 KO versus WT mice at baseline and in response to exercise. There was no significant difference in cardiac output between AC5 KO and WT mice, suggesting AC5 inhibition permits enhanced exercise performance, which is not due to improved cardiac output.

AraAde Increases Exercise Tolerance in Mice Subjected to Chronic Catecholamine Stress Rationale: There are two possible mechanisms by which exercise performance can be enhanced. Increased cardiac output and more efficient utilization of $O_2$ in skeletal muscle. AraAde increases exercise tolerance in mice with HF induced by chronic ISO (FIG. 20). Also, exercise capacity and maximal $O_2$ consumption are increased in AC5 KO, but not cardiac output (FIG. 22). Whether AraAde increases exercise capacity in the presence or absence of HF induced by chronic catecholamine stress will be examined.

The following indices between vehicle and AraAde will be compared:
1) Cardiac output will be measured with chronically implanted aortic flow probe. 2) Exercise capacity with treadmill running test (maximal run distance, work to exhaustion, $VO_2$max/Work, $VCO_2$/Work, RER will be measured and calculated).

Figure 21:
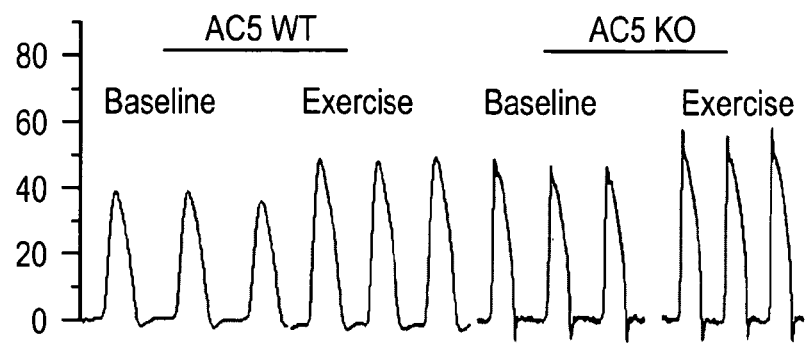
FIG. 21 is a representative recording using a technique of measuring stroke volume and cardiac output in chronically instrumented, conscious mice, using an implanted transonic flow probe on the ascending aorta.

Protocol: Pilot study—The duration of AraAde treatment (15 mg/kg/day, 1-, 2-, 3- and 4-weeks) which provides significant and saturated increase in exercise capacity will be optimized. Mice will be surgically instrumented to measure cardiac output during exercise. (FIGS. 21 and 22).

For HF study—HF will be induced by chronic ISO infusion for 1 week. Followed by treatment with AraAde or vehicle as determined above, mice will be treadmill tested to measure indices defining exercise capacity (maximal run distance, work to exhaustion, $VO_2$max/Work, $VCO_2$/Work, and the respiratory exchange ratio, RER).

Since cardiac output measured via flow probe will also be affected by this cardiac unloading, some measure of isovolumic ventricular contractility will be necessary. Therefore, at the end of exercise in tranquilized mice, we will assess LV function such as LV dP/dt and end-systolic elastance.

Number of Animals: For optimization of AraAde treatment, there are 2 treatment groups (vehicle and AraAde), and 4 groups with 1-, 2-, 3- and 4-weeks of treatment. Two mice will be used in each group. Therefore, 16 mice will be used for this study. For exercise and HF assay, there are 4 groups of mice (vehicle (for ISO)+vehicle (for AraAde), vehicle (for ISO)+AraAde, ISO+vehicle (for AraAde), ISO+AraAde), and 16 mice will be used in each group. Accordingly, 64 mice will be used for the HF study. All together, 80 mice will be used.

Methods

Exercise: Mice will be treadmill-tested to measure indices defining exercise capacity as previously described (Maxwell, et al., *Circulation,* 1998, 98(4): 369-374). All mice will be given one practice trial 3 days before the experiment to adapt to the treadmill-testing environment but otherwise will be kept sedentary. At the time of treadmill testing, each mouse will be placed on a treadmill at a constant 10° angle enclosed by a metabolic chamber through which air flow passes at a constant speed (Oxymax 2, Columbus Instruments). $O_2$ and $CO_2$ gas fractions will be monitored at both the inlet and output ports of the metabolic chamber. After a 30-min period of acclimatization, basal measurements will be obtained over a period of 5 min. The treadmill will then be started at 4 m/min, and the speed will be incrementally increased 2 m/min every 2 min until the mouse reaches exhaustion. The treadmill protocol used in this study, which was chosen on the basis of previous data (Maxwell, et al., *Circulation,* 1998, 98(4): 369-374), was designed so that the mice would quickly attain a plateau, reaching their maximal $VO_2$ before exhaustion. Exhaustion will be defined as spending time (10 sec) on the plate without attempting to reengage the treadmill. $VO_2$, carbon dioxide production ($VCO_2$), and RER will be calculated automatically every 30 sec by the Oxymax system. $VO_2$ and $VCO_2$ will be calculated by taking the difference between the input and output gas flow. RER is calculated as $VCO_2/VO_2$. The maximal value from each mouse will be corrected by the work performed. Work is the product of the vertical running distance to exhaustion and body weight.

Systemic hemodynamics in conscious mice (see FIG. 21): Techniques to measure stroke volume and cardiac output in chronically instrumented, conscious mice, using an implanted transonic flow probe on the ascending aorta, which provides beat by beat measurements of stroke volume, which integrated over time measures cardiac output (the product of heart rate and stroke volume) were recently developed. Systolic, diastolic, mean arterial pressure will be obtained from a catheter (1.4F Millar) implanted in the aorta or via a telemetry system. Cardiac output will be obtained from the transonic flow probe surgically placed in the ascending aorta. Total peripheral resistance will then be calculated via mean arterial pressure, central venous pressure and cardiac output.

Histological Studies, Survival Rate Analysis, Subcutaneous Implantation of Osmotic Pump and Data Analysis and Statistics: These experiments are described in Example 5.

Expected Results: In both the ISO-treated and -untreated group, there will be no difference in cardiac output between vehicle and AraAde. By contrast, mice treated with AraAde will demonstrate enhanced exercise capacity in both the ISO-treated and -untreated group.

EXAMPLE 7

Second generation AC5 inhibitors with better specificity and with minimal adverse effects will be identified. A desirable drug profile will include oral bioavailability and lack of blood brain barrier permeability.

Rationale: A new chemical entity AC5 inhibitor with minimum adverse effects, higher potency and increase selectivity for AC5 than AraAde is desirable. Therefore, second generation AC5 inhibitors with higher efficacy and selectivity for AC5 and improved safety profile will be identified. Purified recombinant AC isoforms are available (Table 1) for screening and characterization purposes. In addition, a high-through put chemiluminescent screening assay using a 386-well microtiter format is available. These increase the feasibility of achieving this Aim.

AC5 KO mice show motor dysfunction reminiscent of Parkinson's disease symptoms (Iwamoto, et al., *J Biol Chem*, 2003, 278(19):16936-16940). This implies that, if an AC5 inhibitor crosses the blood brain barrier (BBB), motor function could be impaired. Drugs lacking BBB permeability will be developed by using the bovine brain microendothelial cell (BBMEC) assay. Furthermore, an oral formulation of the lead inhibitor will be developed because chronic administration is expected when treating obesity and disorders of glucose metabolism.

Protocols: Step 1—To identify optimal side chain(s) in the ribose of AraAde-like compound (Table 2). Step 2—To perform additional screening of a small molecule library for the AC5 inhibitor. Step 3—To identify the most promising AC5 inhibitor, derived from 1) and/or 2), by lead optimization supported by virtual screening studies.

TABLE 2

Schematic representation of side chain modifications of AraAde-related compounds.

Adenine ring with ribose

| Combinations | | Configurations | | | | | | | |
|---|---|---|---|---|---|---|---|---|---|
| | | R1 | R2 | R1 | R2 | R1 | R2 | R1 | R2 |
| R1 | R2 | α | α | α | β | β | α | β | β |
| OH | OH | 1 | | 5 | | 9 (Vidarabine) | | 13 (Adenosine) | |
| OH | H | 2 | | 6 | | 10 | | 14 | |
| H | OH | 3 | | 7 | | 11 | | 15 | |
| H | H | 4 | | 8 = 4 | | 12 = 4 | | 16 = 4 | |

Adenine ring with the substitution for fluorine at 2-carbon with ribose

| Combinations | | Configurations | | | | | | | |
|---|---|---|---|---|---|---|---|---|---|
| | | R1 | R2 | R1 | R2 | R1 | R2 | R1 | R2 |
| R1 | R2 | α | α | α | β | β | α | β | β |
| OH | OH | F1 | | F5 Fidarabine | | F9 | | F13 | |
| OH | H | F2 | | F6 | | F10 | | F14 | |
| H | OH | F3 | | F7 | | F11 | | F15 | |
| H | H | F4 | | F8 = F4 | | F12 = F4 | | F16 = F4 | |

For step 1), a series of AraAde-related compounds with different substitution patterns on the ribose will be synthesized (Table 2). For step 2), about 500 compounds will be screened from a small, targeted library for new AC5 inhibitors. To examine selectivity for AC5, recombinant AC2, AC3, AC5 which represent each distinct major subgroup within the AC family (Iwatsubo, et al., *Endocr Metab Immune Disord Drug Targets*, 2006, 6(3): 239-247) will be used. Recombinant AC6 which is the other major cardiac isoform will be used. A selective AC5 inhibitor must exhibit at least 100-fold selectivity ratio between AC5/AC2, AC5/AC3 and AC5/AC6. Ideally, the new inhibitor $IC_{50}$ will be less than 5 µM. Subsequently, for step 3), a virtual docking study with the most promising hits will be performed, to guide additional medicinal chemistry (Onda, et al., *J Biol Chem*, 2001, 276(51): 47785-47793). Virtual screening assay of an additional 10,000 compounds will be performed and at least an additional 30 compounds for biochemical screening will be selected.

Cell membrane permeability of selected compounds will be tested in H9C2 cells, a cardiac myoblast cell line expressing intracellular AC5. BBB permeability of AC5 inhibitors to select out those with significant BBB penetration by using the BBMEC assay (Pardridge, *J Neurochem*, 1998, 70(5): 1781-1792) will be determined. A medicinal chemist approach will be used to chemically modify potent inhibitors with non-negligible BBB permeability to remove this potential liability (e.g. reduce the number of amide bonds, modify logP and polar surface area). Finally, an oral formulation of the most-promising compound will be contracted out to a CRO with an excellent and demonstrated track-record in pharmaceutical formulation.

Methods:

Overexpression of AC Isoform in Insect Cells: Overexpression of individual recombinant AC2, 3, 5 and 6 will be performed as described previously (Iwatsubo, et al., *J Biol Chem*, 2004, 279(39): 40938-40945; Toya, et al., *J. Mol Cell Cardiol*, 1998, 30(1): 97-108).

AC Assay: Adenylyl cyclase assay will be performed with cAMP Hit Hunter Chemiluminescence Assay (GE healthcare) (Nagakura, et al., *Neurosci Lett*, 2002, 317(2): 69-72) with some modifications. Briefly, membrane preparation of insect cells overexpressing AC subtypes will be incubated in assay buffer in the presence of forskolin (50 µM) for 5 minutes at 37° C. The reaction will be stopped by adding 60% $HClO_4$ and 2.5 M $K_2CO_3$. cAMP production will be examined according to the protocol from the manufacturer.

Virtual Screening Study: Virtual screening will be performed as previously described (Onda, et al., *J Biol Chem*, 2001, 276(51): 47785-47793), based on the interaction of an adenine analogue with AC (Tesmer, et al., *Biochemistry*, 2000, 39(47): 14464-14471).

cAMP Accumulation Assay in H9C2 Cells: Cell culture and cAMP accumulation assays in H9C2 cells will be performed with [$^3$H]adenine as we preciously described (Iwatsubo, et al., *J Biol Chem*, 2004, 279(39): 40938-40945).

BBMEC Permeability Assay: This assay will be performed as previously described (Pardridge, *J Neurochem*, 1998, 70(5): 1781-1792). Isolated BBMEC from bovine brain will be maintained in minimal essential media (MEM). By using radiolabeled compounds, transport studies will be conducted in side-by-side chambers for 60 min. Permeability determinations will be also made in order to have a basis of comparison. Since AraAde has little brain permeability into the BBB (Brink, et al., *Cancer Res*, 1964; 24: 1042-1049), and little effect on motor function, a compound that has less BBMEC permeability than AraAde will be used.

Data Analysis and Statistics: Statistical comparisons among compound group and control will be calculated using one-factor ANOVA with Bonferroni post hoc test. P values of <0.05 will be considered significant.

EXAMPLE 8

The duration of ISO treatment will be optimized(2.5 mg/kg/d (Rona, et al., *Rev Can Biol*, 1959 18(1): 83-94) for 1-, 2-, 3- and 4-weeks), to provide the following hemodynamic endpoints; LVEDP is greater than 20 mmHg, LV dP/dt is less than 1600 mmHg/sec, and EF is less than 40%, in chronically instrumented dogs (Shen, et al., *Circulation*, 1999; 100(20): 2113-2118; Ishikawa, et al., *J Clin Invest*, 1994; 93(5): 2224-2229; Vatner, et al., *J Clin Invest*, 1985; 76(6): 2259-2264).

Obesity, Glucose Metabolism and HF Studies: Dogs will be fed a high-fat diet for 6 months to induce obesity. A previous study demonstrated that a 12-week high fat diet induces disorders of glucose metabolism in beagles (Tsunoda, et al., *Am J Physiol Endocrinol Metab*, 2008; 294 (5): E833-840). Two months after the initiation of a high-fat-diet, dogs will be then subjected to AC5 inhibitor treatment. ISO will be chronically administered for the optimized treatment period as determined above. Body weight, food intake, fasting blood glucose, insulin and triglyceride levels will be monitored on a weekly basis. Glucose tolerance test will be performed on a monthly basis. Regular standard hematological and biochemical studies will be performed in blood samples on a monthly basis to check for abnormalities in hematology, liver and kidney function.

Number of Animals: For optimization of the duration of ISO treatment, 2 dogs with chronic instrumentation for monitoring changes in cardiac function will be used. For obesity, glucose metabolism and HF assay, there are 2 groups of dogs (vehicle+ISO, AC5 inhibitor+ISO) and 8 dogs will be used in each group for a total of 16 dogs. Altogether, 18 dogs will be used.

Dogs: Beagles will be used in this study according to a previous high-fat diet studies (Tsunoda, et al., *Am J Physiol Endocrinol Metab*, 2008; 294(5): E833-840). Experiments will be performed in 5 month-old male beagles (n=8/group, 18-22 BW). Surgical implantation of instrumentation will be performed as previously described (Shen, et al., *Circulation*, 1999; 100(20): 2113-2118; Ishikawa, et al., *J Clin Invest*, 1994; 93(5): 2224-2229; Vatner, et al., *J Clin Invest*, 1985; 76(6): 2259-2264; Hittinger, et al., *Circulation*, 1994; 89(5): 2219-2231; Hittinger, et al., *Circ Res*, 1990; 66(2): 329-343). Briefly, under anesthesia, two polyvinyl catheters (Tygon, Norton Plastics) will be inserted into the proximal descending thoracic aorta. The pericardium will be then incised longitudinally, and additional catheters will be inserted into the proximal main pulmonary artery and into the left atrium through the left atrial appendage. All four catheters will be passed through the interscapular space and exteriorized at the back of the neck by using a hollow knitting needle. ISO will be given (i.v.) through the implanted Tygon catheter connected to mini-infusion pump carried in a vest worn by the dog. ISO (2.5 mg/kg/d) (Rona, et al., *Rev Can Biol*, 1959; 18(1): 83-94) will be dissolved in normal saline and continuously infused. The AC5 inhibitor identified in Example 7 will be orally administered.

Diets: Based on publicly available data in beagles (Tsunoda, et al., *Am J Physiol Endocrinol Metab*, 2008, 294 (5): E833-840), the high-fat diet will be prepared by mixing the standard diet (Oriental Yeast Co.) with 20% (wt/wt) beef tallow and 20% (wt/wt) skim milk. Caloric distribution in the high-fat diet (4,613 kcal/kg) will be 48% fat, 34% carbohydrate, and 18% protein. The animals will be allowed access to chow and tap water ad libitum and will be housed individually in stainless steel cages.

Body Weight and Food Measurements, Blood Glucose, Insulin and Triglycerides, Glucose Tolerance Test, Histological Studies, and Data Analysis and Statistics: These studies are described in Example 5.

Expected Results: The new AC5 inhibitor will ameliorate the development of remodeling after chronic catecholamine stress as well as reduce obesity and improve glucose metabolism. After chronic ISO infusion, the new AC5 inhibitor will show: 1) better cardiac function (lower LVEDP, higher LV dP/dt and LVEF), 2) lower myocardial apoptosis, and 3) reduced cardiac fibrosis. Before and after chronic ISO treatment, the AC5 inhibitor will show 4) lower fasting blood glucose, 5) lower plasma insulin level, 6) lower plasma triglyceride levels, 7) improved glucose tolerance and 8) lower ratio of body weight to food intake, compared to vehicle.

I claim:

1. A method of treating obesity comprising administering a pharmaceutically effective amount of at least one compound capable of inhibiting AC5 to a patient.

2. A method according to claim 1 wherein the AC5 inhibiting compound is 9-β-9-β-arabinofuranosyladenine (AraAde).

3. A method according to claim 1 wherein the AC5 inhibiting compound is administered in an amount of about 1 to about 100 mg/kg/day.

4. A method according to claim 1 wherein the AC5 inhibiting compound is administered in an amount of about 10 to about 40 mg/kg/day.

5. A method according to claim 1 wherein the AC5 inhibiting compound is administered in an amount of about 15 to about 25 mg/kg/day.

6. The method of claim 1 wherein the compound is administered parenterally.

7. A method of treating diabetes mellitus comprising administering a pharmaceutically effective amount of at least one compound capable of inhibiting AC5 to a patient.

8. A method according to claim 7 wherein the AC5 inhibiting compound is 9-β-9-β-arabinofuranosyladenine (AraAde).

9. A method according to claim 7 wherein the AC5 inhibiting compound is administered in an amount of about 1 to about 100 mg/kg/day.

10. A method according to claim 7 wherein the AC5 inhibiting compound is administered in an amount of about 10 to about 40 mg/kg/day.

11. A method according to claim 7 wherein the AC5 inhibiting compound is administered in an amount of about 15 to about 25 mg/kg/day.

12. The method of claim 7 wherein the compound is administered parenterally.

* * * * *